(12) United States Patent
Lassalle et al.

(10) Patent No.: US 8,623,893 B2
(45) Date of Patent: Jan. 7, 2014

(54) PYRIDINO-PYRIDINONE DERIVATIVES, PREPARATION AND THERAPEUTIC USE THEREOF

(75) Inventors: Gilbert Lassalle, Paris (FR); Valérie Martin, Paris (FR); Gary McCort, Paris (FR); Cécile Volle-Challier, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/477,778

(22) Filed: May 22, 2012

(65) Prior Publication Data

US 2013/0005724 A1 Jan. 3, 2013

Related U.S. Application Data

(63) Continuation of application No. PCT/FR2010/052480, filed on Nov. 22, 2010.

(30) Foreign Application Priority Data

Nov. 23, 2009 (FR) ...................................... 09 05602

(51) Int. Cl.
*A61K 31/04* (2006.01)
*C07D 215/38* (2006.01)

(52) U.S. Cl.
USPC .......................................... 514/312; 546/159

(58) Field of Classification Search
USPC .......................................... 546/159; 514/312
See application file for complete search history.

(56) References Cited

U.S. PATENT DOCUMENTS

| | | | |
|---|---|---|---|
| 8,263,614 | B2 | 9/2012 | Alam et al. |
| 8,436,011 | B2 | 5/2013 | Bellevergue et al. |
| 8,470,847 | B2 | 6/2013 | Alam et al. |
| 2013/0178472 | A1 | 7/2013 | Bellevergue et al. |

FOREIGN PATENT DOCUMENTS

| EP | 2524915 | * 11/2012 |
|---|---|---|
| FR | 2917412 | 12/2008 |
| FR | 2917413 | 12/2008 |
| WO | WO 2005/026156 | 3/2005 |
| WO | WO 2008/121687 | 10/2008 |
| WO | WO 2010/004197 | 1/2010 |

OTHER PUBLICATIONS

Abramsson, at al., Endothelial and nonendothelial sources of PDGF-B regulate pericyte recruitment and influence vascular pattern formation in tumors, J. Clin. Invest 112, 1142-1151, (2003).
Aono, et al., Imatinib as a novel antifibrotic agent in bleomycin-induced pulmonary fibrosis in mice, Am. J. Respir. Crit Care Med. 171, 1279-1285, (2005).
Apte, et al., Targeting the platelet-derived growth factor receptor in antivascular therapy for human ovarian carcinoma, Clin. Cancer Res. 10, 897-908, (2004).
Bergers, et al., Benefits of targeting both pericytes and endothelial cells in the tumor vasculature with kinase inhibitors, J. Clin. Invest 111, 1287-1295, (2003).
Bonner, Regulation of PDGF and its receptors in fibrotic diseases, Cytokine Growth Factor Rev. 15, 255-273, (2004).
Borkham-Kamphorst, et al., Pro-fibrogenic potential of PDGF-D in liver fibrosis, J. Hepatol. 46, 1064-1074, (2007).
Bouzin, et al., Targeting tumor stroma and exploiting mature tumor vasculature to improve anti-cancer drug delivery, Drug Resist. Updat. 10, 109-120, (2007).
Cao, Direct role of PDGF-BB in lymphangiogenesis and lymphatic metastasis, Cell Cycle 4, 228-230, (2005).
Cao, et al., Angiogenesis stimulated by PDGF-CC, a novel member in the PDGF family, involves activation of PDGFR-alphaalpha and -alphabeta receptors, FASEB J. 16, 1575-1583, (2002).
Carow, et al., Expression of the hematopoietic growth factor receptor FLT3 (STK-1/Flk2) in human leukemias, Blood 87, 1089-1096, (1996).
Chin, et al., K252a inhibits proliferation of glioma cells by blocking platelet-derived growth factor signal transduction, Clin. Cancer Res. 3, 771-776, (1997).
Claesson-Welsh, Platelet-derived growth factor receptor signals, J. Biol. Chem. 269, 32023-32026, (1994).
Corless, et al., Biology of gastrointestinal stromal tumors, J. Clin. Oncol. 22, 3813-3825, (2004).
Corless, et al., PDGFRA mutations in gastrointestinal stromal tumors: frequency, spectrum and in vitro sensitivity to imatinib, J. Clin. Oncol. 23, 5357-5364, (2005).
Deguchi, et al., Inhibitory effects of trapidil on PDGF signaling in balloon-injured rat carotid artery, Life Sci. 65, 2791-2799, (1999).
Eitner, et al., Expression of a novel PDGF isoform, PDGF-C, in normal and diseased rat kidney, J. Am. Soc. Nephrol. 13, 910-917, (2002).
Eitner, et al., PDGF-C is a proinflammatory cytokine that mediates renal interstitial fibrosis, J. Am. Soc. Nephrol. 19, 281-289, (2008).
Ferns, et al., Inhibition of neointimal smooth muscle accumulation after angioplasty by an antibody to PDGF, Science 253, 1129-1132, (1991).

(Continued)

Primary Examiner — D M Seaman

(57) ABSTRACT

The present invention relates to derivatives of pyridino-pyridinones, and to their preparation and use thereof, having activity as inhibitors of kinase activity of receptors for PDGF (platelet derived growth factors) ligands and optionally of receptors for the FLT3 (fms-like tyrosine kinase receptor) ligand receptors, said derivatives comprising compounds of formula (I):

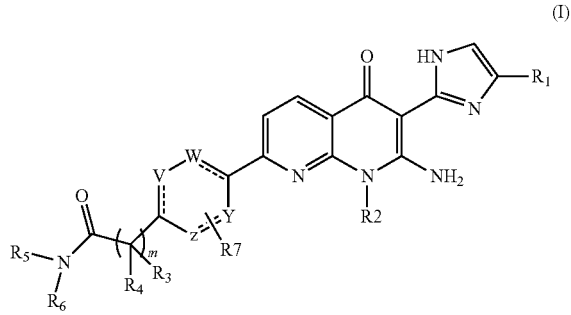

wherein the various substituent groups are more specifically defined herein. The compounds are suitable as therapeutics for the treatment of various proliferative diseases.

24 Claims, No Drawings

(56) References Cited

OTHER PUBLICATIONS

Eons, et al., VEGF-R2 and neuropilin-1 are involved in VEGF-A-induced differentiation of human bone marrow progenitor cells, J. Cell Physiol 200, 351-359, (2004).
Geng, et al., STI571 (Gleevec) improves tumor growth delay and survival in irradiated mouse models of glioblastoma, Int. J. Radiat. Oncol. Biol. Phys. 64, 263-271, (2006).
Griffin, et al., Discovery of a fusion kinase in EOL-1 cells and idiopathic hypereosinophilic syndrome, Proc. Natl. Acad. Sci. U. S. A 100, 7830-7835, (2003).
Griffon-Etienne, et al., Taxane-induced apoptosis decompresses blood vessels and lowers interstitial fluid pressure in solid tumors: clinical implications, Cancer Res. 59, 3776-3782, (1999).
Heldin, Structural and functional studies on platelet-derived growth factor, EMBO J. 11, 4251-4259, (1992).
Hellstrom, et al., Lack of pericytes leads to endothelial hyperplasia and abnormal vascular morphogenesis, J. Cell Biol. 153, 543-553, (2001).
Hellstrom, et al., Role of PDGF-B and PDGFR-beta in recruitment of vascular smooth muscle cells and pericytes during embryonic blood vessel formation in the mouse, Development 126, 3047-3055, (1999).
Heuchel, et al., Platelet-derived growth factor beta receptor regulates interstitial fluid homeostasis through phosphatidylinositol-3' kinase signaling, Proc. Natl. Acad. Sci. U. S. A 96, 11410-11415, (1999).
Hwang, et al., Inhibition of platelet-derived growth factor receptor phosphorylation by STI571 (Gleevec) reduces growth and metastasis of human pancreatic carcinoma in an orthotopic nude mouse model, Clin. Cancer Res. 9, 6534-6544, (2003).
Kelly, at al., FLT3 internal tandem duplication mutations associated with human acute myeloid leukemias induce myeloproliferative disease in a murine bone marrow transplant model, Blood 99, 310-318, (2002).
Kim, et al., Simultaneous blockade of platelet-derived growth factor-receptor and epidermal growth factor-receptor signaling and systemic administration of paclitaxel as therapy for human prostate cancer metastasis in bone of nude mice, Cancer Res. 64, 4201-4208, (2004).
Le Tourneau, et al., Sunitinib: a novel tyrosine kinase inhibitor. A brief review of its therapeutic potential in the treatment of renal carcinoma and gastrointestinal stromal tumors (GIST), Ther. Clin. Risk Manag. 3, 341-348, (2007).
Levis, et al., Novel FLT3 tyrosine kinase inhibitors, Expert. Opin. Investig. Drugs 12, 1951-1962, (2003).
Lindner, Expression of platelet-derived growth factor ligands and receptors by rat aortic endothelium in vivo, Pathobiology 63, 257-264, (1995).
Merchant, et al., Potential use of imatinib in Ewing's Sarcoma: evidence for in vitro and in vivo activity, J. Natl. Cancer Inst. 94, 1673-1679, (2002).
Mizuki, et al., Flt3 mutations from patients with acute myeloid leukemia induce transformation of 32D cells mediated by the Ras and STAT5 pathways, Blood 96, 3907-3914, (2000).
Neef, et al., Oral imatinib treatment reduces early fibrogenesis but does not prevent progression in the long term, J. Hepatol. 44, 167-175, (2006).
Pietras, et al., Functions of paracrine PDGF signaling in the proangiogenic tumor stroma revealed by pharmacological targeting, PLoS. Med. 5, e19, (2008).
Pietras, et al., Inhibition of PDGF receptor signaling in tumor stroma enhances antitumor effect of chemotherapy, Cancer Res. 62, 5476-5484, (2002).
Pietras, et al., PDGF receptors as cancer drug targets, Cancer Cell 3, 439-443, (2003).
Ritchie, et al., The Tel-PDGFRbeta fusion gene produces a chronic myeloproliferative syndrome in transgenic mice, Leukemia 13, 1790-1803, (1999).
Rosnet, et al., Human FLT3/PLK2 gene: cDNA cloning and expression in hematopoietic cells, Blood 82, 1110-1119, (1993).
Ross, Platelet-derived growth factor, Annu. Rev. Med, 38, 71-79, (1987).
Rovida, et al., ERK5 differentially regulates PDGF-induced proliferation and migration of hepatic stellate cells, J. Hepatol. 48, 107-115, (2008).
Schermuly, et al., Reversal of experimental pulmonary hypertension by PDGF inhibition, J. Clin. Invest 115, 2811-2821, (2005).
Sirois, et al., Antisense oligonucleotide inhibition of PDGFR-beta receptor subunit expression directs suppression of intimal thickening, Circulation 95, 669-676, (1997).
Sjoblom, et al., Growth inhibition of dermatofibrosarcoma protuberans tumors by the platelet-derived growth factor receptor antagonist STI571 through induction of apoptosis, Cancer Res. 61, 5778-5783, (2001).
Strawn, et al., Inhibition of glioma cell growth by a truncated platelet-derived growth factor-beta receptor, J. Biol. Chem. 269, 21215-21222, (1994).
Tse, et al., Constitutive activation of FLT3 stimulates multiple intracellular signal transducers and results in transformation, Leukemia 14, 1766-1776, (2000).
Uehara, et al., Effects of blocking platelet-derived growth factor-receptor signaling in a mouse model of experimental prostate cancer bone metastases, J. Natl. Cancer Inst. 95, 458-470, (2003).
Ullrich, et al., Signal transduction by receptors with tyrosine kinase activity, Cell 61, 203-212, (1990).
Uren, et al., Beta-platelet-derived growth factor receptor mediates motility and growth of Ewing's sarcoma cells, Oncogene 22, 2334-2342, (2003).
Weiss, et al., Switching signals on or off by receptor dimerization, Cell 94, 277-280, (1998).
Yu, et al., Platelet-derived growth factor (PDGF) receptor-alpha-activated c-Jun NH2-terminal kinase-1 is critica for PDGF-induced p21WAF1/CIP1 promoter activity independent of p53, J. Biol. Chem. 278, 49582-49588, (2003).
Yu, et al., Platelet-derived growth factor signaling and human cancer, J. Biochem. Mol. Biol. 36, 49-59, (2003).
Zwerner, et al., PDGF-C is an EWS/FLI induced transforming growth factor in Ewing family tumors, Oncogene 20, 626-633, (2001).
Drexler, Expression of FLT3 receptor and response to FLT3 ligand by leukemic cells, Leukemia 10, 588-599 (1996).
McArthur, Molecular targeting of dermatofibrosarcoma protuberans: a new approach to a surgical disease, J. Natl. Compr. Canc. Netw. 5, 557-562, (2007).
Medeiros, et al., KIT-negative gastrointestinal stromal tumors: proof of concept and therapeutic implications, Am. J. Surg. Pathol. 28, 889-894, (2004).
Stacchini, et al., Expression of type III receptor tyrosine kinases FLT3 and KIT and responses to their ligands by acute myeloid leukemia blasts, Leukemia 10, 1584-1591, (1996).
Ishikawa, et al., Preparation of Carboxylic Acid Fluorides Using Hexafluoro-1,2-Epoxypropane, Chem. Lett., (1976) pp. 1407-1408.
International Search Report for WO2011/061458 dated May 26, 2011.
Carroll, of al., The TEL/Platelet-Derived Growth Factor B Receptor (PDGFBR) Fusion in Chronic Myelomonocytic Leukemia is a Transforming Protein That Self-Associates and Activates PDGFBR Kinase-Dependent Signaling Pathways, Proc. Natl. Acad. Sci. USA, vol. 93, pp. 14845-14850, (1996).
Cools, et al., The EOL-1 Cell Line as an In Vitro Model for the Study of FIP1L1-PDGFRA-Positive Chronic Eosinophilic Leukemia, Blood, vol. 103, No. 7, (2004), pp. 2802-2805.
Fukushima, et al., Synthesis and Structure-Activity Relationships of Potent 3- and 4-Substituted-2-Cyanoprrolidine Dipeptidyl Peptidase IV Inhibitors, Bioorganic & Medicinal Chemistry, vol. 12, (2004), pp. 6053-6061.
Giroux, et al., One Pot Biaryl Synthesis via in Situ Boronate Formation, Tetrahedron Letters, vol. 38, No. 22, pp. 3841-3844, (1997).
Vuorinen, et al., Imatinib Mesylate Inhibits Fibrogenesis in Asbestos-Induced Interstitial Pneumonia, Experimental Lung Research, vol. 33, pp. 357-373, (2007).

(56) References Cited

OTHER PUBLICATIONS

Jones, et al., Triazolopyridines. 18.1 Nucleophilic Substitution Reactions on Triazolopyridines; A New Route to 2,2'-Bipyridines, Tetrahedron, vol. 53, No. 24, pp. 8257-8268, (1997).
O'Farrell, et al., SU11248 is a Novel FLT3 Tyrosine Kinase Inhibitor With Potent Activity In Vitro and In Vivo, Blood, (2003), vol. 101, No. 9, pp. 3597-3605.
Olah, et al., Synthetic Methods and Reactions; IV. Fluorination of Carboxylic Acids with Cyanuric Fluoride, Synthesis, (1973) pp. 487-488.
Spiekermann, et al., The Protein Tyrosine Kinase Inhibitor SU5614 Inhibits FLT3 and Induces Growth Arrest and Apoptosis in AML-Derived Cell Lines Expressing a Constitutively Activated FLT3, Blood, vol. 101, No. 4, (2003), pp. 1494-1504.
Supuran, et al., Protein Tyrosine Kinase Inhibitors as Anticancer Agents, Expert Opin. Ther. Patents, (2004), vol. 14, No. 1, pp. 35-53.
Mukaiyama, et al., A Convenient Method for the Preparation of Carboxylic Acid Fluorides, Chem. Lett., (1976) pp. 303-306.
Ishiyama, et al., Palladium(o)-Catalyzed Cross-Coupling Reaction of Alkoxydibron With Haloarenes: A Direct Procedure for Arylboronic Esters, J. Org. Chem., vol. 60, pp. 7508-7510, (1995).
Stille, et al., Stereospecific Cross-Coupling of Vinyl Halides With Vinyl Tin Reagents Catalyzed by Palladium, J. Am. Chem. Soc., vol. 109, pp. 813-817, (1987).
Miyaura, et al., Palladium-Catalyzed Cross-Coupling Reactions of Organoboron Compounds, Chem Rev., 1995 (95) 7 pp. 2457-2483.
Van Leusen, et al., One-Step Conversion of Aldehydes to Nitriles. Introduction of a One-Carbon Unit, Synthetic Communications, vol. 10, No. 5, pp. 399-403, (1980).
Whitten, et al., [2-Trimethylsily)Ethoxy]Methyl (SEM) as a Novel and Effective Imidazole and Fused Aromatic Imidazole Protecting Group, J. Org. Chem., (1986), vol. 51, pp. 1891-1894.
Kaur, et al., Corneal Stroma PGDF Blockade and Myofibroblast Development, Experimental Eye Research, vol. 88, (2009), pp. 960-965.
Jo, et al., Inhibition of Platelet-Derived Growth Factor B Signaling Enhances the Efficacy of Anti-Vascular Endothelial Growth Factor Therapy in Multiple Models of Ocular Neovascularization, American Journal of Pathology, vol. 168, No. 6, (2006), pp. 2036-2053.
Dell, et al., The Role pf PDGF Receptor Inhibitors and PI3-Kinase Signaling in the Pathogenesis of Corneal Neovascularization, Investigative Ophthalmology & Visual Science, (2006), vol. 47, No. 5, pp. 1928-1937.
Dorwald, Side Reactions in Organic Synthesis: A Guide to Successful Synthesis Design, 2005, Wiley, Wienheim, Chapter 1.
Wermuth, Practice of Medicinal Chemistry, Third Edition, 2008, Elsevier, pp. 126, 313, and 320-323.
Godard, A., et al., Synlett (1994) 4, 235-236.
C. Doerig, L. Meijer, and J. C. Mottram, Trends in Parasitology (2002) 18, 366-371.

* cited by examiner

PYRIDINO-PYRIDINONE DERIVATIVES, PREPARATION AND THERAPEUTIC USE THEREOF

CROSS-REFERENCE TO RELATED APPLICATIONS

This application is a continuation of International Patent Application No. PCT/FR2010/052480, filed Nov. 22, 2010, the entire contents of which are expressly incorporated herein by reference, which claims the benefit of priority of French patent application Ser. No. 09/05602, filed Nov. 23, 2009.

BACKGROUND OF THE INVENTION

The present invention relates to derivatives of pyridino-pyridinones substituted (i) in position 3 with an imidazole, itself substituted with a group R1 and substituted (ii) in position 7 with an aryl or heteroaryl, itself substituted optimally with a motif of the type —[C(R3)(R4)]$_m$—CO—N(R5)(R6), to the preparation thereof and to the application thereof in therapeutics as inhibitors of kinase activity of receptors for PDGF (platelet derived growth factors) ligands and optionally of receptors for the FLT3 (fms-like tyrosine kinase receptor) ligand.

The FLT3 and PDGF-R receptors are members of class III of the family of tyrosine kinase receptors (TKR), which also includes the stem cell factor receptor (c-kit) and M-CSF receptor (c-fms). They are characterized by an extracellular domain composed of 5 immunoglobulin-like domains containing the ligand binding region, a transmembrane domain, and an intracellular moiety composed of a juxtamembrane domain, a kinase domain split in two by an insert domain (split domain) (Ullrich & Schlessinger, 1990). The fixation of ligands on the TKR induces dimerization of the receptors, and activation of their tyrosine kinase moiety which leads to transphosphorylation of tyrosine residues (Weiss & Schlessinger, 1998). These phosphorylated residues thus serve as a point of anchorage for the intracellular signalling proteins which in fine cause various cellular responses: maintenance, division, proliferation, differentiation, or even cellular migration. (Claesson-Welsh, 1994).

The gene coding for FLT3 is located on chromosome 13q12 (Rosnet et al., 1992) and codes for the FLT3 protein (CD135 antigen) expressed specifically by the haematopoietic cells and more particularly the immature cells such as haematopoietic stem cells and myeloid and lymphoid multipotent progenitors and its expression disappears in the course of haematopoietic differentiation. Its ligand, the FLT3 Ligand, induces dimerization of the receptor, followed by autophosphorylation of the intracellular moiety of the receptor which leads to activation of the signalling cascade. The effects of activation of the receptor by its ligand are the survival and expansion of the multipotent progenitors.

Two isoforms of receptors to the PDGFs have been identified, the chain PDGF-Ralpha and the chain PDGF-Rbeta, which following fixation of their ligands are homo- or heterodimerized and induce intracellular signalling. The receptors to the PDGFs are essentially expressed by the cells of mesenchymatous origin and are notably found on fibroblasts, smooth muscle cells, pericytes and glial cells (Ross et al., 1986, Heldin, 1992).

Platelet Derived Growth Factor, PDGF, a protein with a molecular weight of about 30 000 dalton, is secreted essentially by the platelets, and secondarily by the endothelium, vascular smooth muscles and monocytes. It is formed from two polypeptide chains joined together by disulphide bridges forming either homodimers, or heterodimers. Four genes (7p22, 22q13, 4q31 and 11q22) have been described as coding for 4 different polypeptide chains (A, B, C and D), which once dimerized give five biologically active ligands PDGF-AA, BB, CC, DD and AB (for review, Yu et al., 2003). There is specificity of binding, including notably PDGF-AA for the alpha isoform of the receptor, PDGF-D for the BB form, and PDGF-C for the alpha and alpha/beta form. The PDGF ligands are potent mitogens, but are also involved in phenomena of migration, survival, apoptosis and cellular transformation.

SUMMARY OF THE INVENTION

The present invention relates to derivatives of pyridino-pyridinones, and to their preparation and use thereof, having activity as inhibitors of kinase activity of receptors for PDGF (platelet derived growth factors) ligands and optionally of receptors for the FLT3 (fms-like tyrosine kinase receptor) ligand receptors, said derivatives comprising compounds of formula (I):

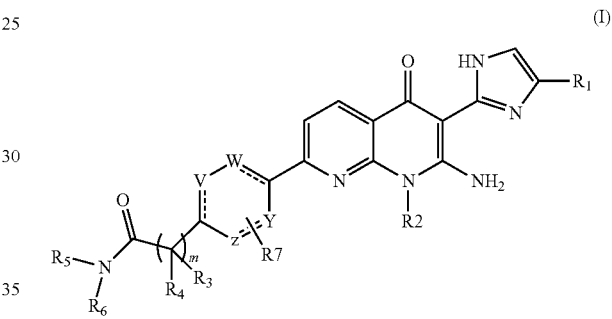

wherein the various substituent groups are more specifically defined herein. The compounds are suitable as therapeutics for the treatment of various proliferative diseases.

DETAILED DESCRIPTION OF THE INVENTION

Inhibitors of the PDGF-R alpha, beta and FLT3 function are involved in various therapeutic areas. The physiopathological phenomena in which these receptors may be involved, and therefore therapeutic areas of interest in which the compounds of the invention may be employed, include liquid cancers or leukaemias, solid cancers with or without metastases targeting tumour cells and/or cells of the tumour environment (vascular, fibroblastic), fibroses and vascular diseases:

A. Liquid Cancers

The leukaemias are of various types and affect either the myeloid compartment or the lymphoid compartment.

Expression of FLT3 in leukaemic cells derived from acute myeloid leukaemias (AML) is of the order of 100% of cases, and FLT3 thus contributes to stimulation of survival and proliferation of leukaemic cells (Carow et al., 1996; Drexler et al., 1996, Stacchini et al., 1996).

Moreover, FLT3 is the site of activating mutations in 22 to 30% of adult AMLs and 11% of childhood AMLs. Most often it involves in-tandem duplications (ITD) in the transmembrane region of the receptor (more particularly exons 14 and 15). These mutations conserve the reading frame and their size can vary between 18 and 111 base pairs. More rarely in about 7% of AMLs, a point mutation is found on the D835 residue located in the kinase domain. In the majority of cases, the FLT3 ITD forms have a greater risk of relapse and are markers of low survival prognosis. These two types of mutations lead to constitutive activity of the kinase domain independent of stimulation by the ligand and have been shown to transform haematopoietic cells in vitro and in vivo (Mizuki et al., 2000; Tse et al., 2000). Kelly et al., (2002) gave an elegant demonstration, in a model of bone marrow reconstitution in the mouse, that FLT3 ITD causes a myeloproliferative syndrome.

The advantage of using inhibitors of tyrosine kinase activity has been reported both in vitro and in vivo by several teams, and recently in the model of bone marrow reconstitution FLT3 ITD, such an inhibitor was shown to be capable of inducing regression of the tumour and of increasing the survival rate of the animals (Ofarrel, 2003).

Moreover, recent data demonstrate the advantage of combining said inhibitors with cytotoxic agents such as daunorubicin (Levis et al., 2004).

Interestingly, blast cells of the AML type can also overexpress other receptors with kinase activity such as c-kit or even PDGF-R.

Myeloproliferative/Dysplastic Syndromes

Quite frequently, cytogenetic abnormalities resulting from chromosomal translocations have been reported in myeloproliferative syndromes. These rearrangements generate deregulated fusion proteins with tyrosine kinase activity involved in the proliferation of myeloid blast cells.

Fusion Proteins with Kinase Activity PDGF-R Beta

The fusion proteins with kinase activity PDGF-R beta are constituted of the intracellular moiety of PDGF-R-beta and in addition a domain N-ter of another protein (generally a transcription factor). The following have been reported notably in chronic myelomonocytic leukaemias (CMML): RabS/PDGF-Rbeta, H4-PDGF-Rbeta, HIP1-PDGF-RB or Tel/PDGF-R beta. The latter is the most represented. It is derived from the translocation t(5; 12)(q31; p12) and codes for a fusion protein constituted of the N-terminal part of the transcription factor Tel and the C-terminal part of PDGF-Rbeta. An oligomerization domain present in the Tel part leads to a dimerized form of the fusion protein and to the constitutive activity of the kinase domain. This protein has been shown in vitro to be capable of transforming haematopoietic cells on many occasions and notably in detail in the article by M. Carrol et al. (PNAS, 1996, 93, 14845-14850). In vivo, this fusion protein leads to a hyperproliferation syndrome of the myeloid cells (Ritchie et al., 1999).

Moreover, in animals, and in clinical practice in humans, it has been shown that inhibitors of tyrosine kinase activity inhibit the proliferation of blast cells and can halt the process of leukemogenesis.

Fusion Proteins with Kinase Activity PDGF-R Alpha

Two fusion proteins involving PDGF-R alpha have been reported: bcr-PDGF-Ralpha present in an atypical chronic myeloid leukaemia (CML) and FIP1L1-PDGF-Ralpha found in a subpopulation of leukaemias, the LEC "eosinophilic leukaemias", arising from a hyper-eosinophilia syndrome (Griffin et al., 2003). This fusion protein bears constitutive activity of the kinase domain of PDGF-R alpha and is responsible for the anarchic proliferation of these cells.

Inhibitors of the kinase activity of PDGF-R alpha have shown efficacy on the proliferation of FIP1L1-PDGF-R alpha positive cells and recently an inhibitor compound has received the indication for HES/CEL.

Thus, inhibiting the kinase activity of PDGF-Ralpha and beta and the FLT3 wt and FLT3ITD activity, as is done by the compounds of the invention, proves to be of therapeutic interest for AMLs.

Apart from AMLs and myeloproliferative syndromes, other leukaemias can be interesting for targeting with such inhibitors, including B-ALL and T-ALL (acute lymphoid-B or lymphoid-T leukaemias), where FLT3 is also expressed. Moreover, by virtue of normal expression of FLT3 on haematopoietic stem cells and the demonstration of its expression on leukaemic stem cells, inhibitors of the kinase activity of FLT3 might prove beneficial in all leukaemias (including the CMLs) where the role of leukaemic stem cells in relapse where resistance is involved.

B. Solid Cancers

Inhibitors of the tyrosine kinase activity of the PDGF-R alpha and beta receptors may be of interest for solid cancers either by directly targeting the tumour cell, which through an autocrine or paracrine mechanism is sensitive to the TK inhibitory activity of PDGF-R, or by targeting cells in the surroundings by destabilizing the network for promoting combination with other therapeutic agents.

Examples of Solid Cancers in which the Target is the Tumour Cell

Soft Cancer: Ewing Sarcoma

Ewing sarcoma is a form of bone cancer which mainly affects children and young adults (the average age is 13 years). It covers 10% of primary bone tumours and the risk of metastasis is high. It is a rare tumour affecting 2 to 3 persons per million inhabitants per year. The tumour cells are characterized by a chromosomal translocation t(11; 22) coding for the fusion protein EWS/FLI1.

The cells responsible are those of the mesenchyma, which express the PDGF-R-beta receptor which induces the motility and growth of the Ewing sarcoma cells under stimulation by PDGF-BB (Üren et al., 2003). Moreover, Zwerner and May (2001) have demonstrated expression of PDGF-C by the Ewing sarcoma cells.

These same cells also express the receptor TKR c-kit and it has been shown that an inhibitor of the kinase activity of PDGF-R and c-kit is capable of inhibiting tumour growth of Ewing sarcoma lines in a mouse model of xenograft (Merchant et al., 2002).

Tumour of Connective Tissue (Gist, Dermatofibrosarcoma)

GISTs (Gastrointestinal Stromal Tumours)

Fletcher's group (2004) considered the 15% of GISTs in which KIT is neither mutated nor overexpressed (KIT-wt). These authors observed strong overexpression of the PDGF-R alpha receptor. This situation is encountered in about a third of these GIST KIT-wt. As for mutations of PDGFRA, the authors observe them (35%) in cases where KIT is normal. Mutated PDGFRAs have high tyrosine kinase activity and are constitutive and affect aspartic acid in position 842. In the same way as for Ewing sarcomas, two inhibitors of the kinase activity of c-kit and PDGF-R have shown efficacy in vitro and in vivo on the proliferation of PDGF-Ralpha mutated cells (Le Tourneau et al., 2007; Corless et al., 2005).

dermatofibrosarcomas (of Darier and Ferrand or protuberans or DFSP)

Darier and Ferrand dermatofibrosarcoma (or DFSP) is a skin tumour with fusiform cells of intermediate malignity characterized by slow progression with a major risk of recurrence in the case of insufficient exeresis. A genetic abnormality present in 95% of cases was discovered in 1990, notably with identification of the translocation of chromosomes 17 and 22 t(17-22)(q22; q13) which leads to fusion of genes COL1A1 and PDGF B and a large amount of PDGFB overexpresses its tyrosine kinase receptor, PDGFR. Inhibiting the kinase activity of PDGF-R is a promising therapy since this leads in vitro to inhibition of proliferation and apoptosis of tumour cells and in vivo this permits reduction of tumour growth in models of tumour grafting in immunodeficient mice (Sjöblom T et al., 2001). Moreover, clinical studies have demonstrated the efficacy (complete or total remission) of such a molecule in DFSPs (for review see McArthur, 2007).

Gliomas and Glioblastomas:

Glioblastoma is the commonest brain tumour and the most aggressive with a median survival of around 1 year. PDGFs and their receptors (alpha and beta) are frequently expressed in gliomas. The possibility exists that an autocrine/paracrine loop may contribute to the pathogenicity of these tumours. The PDGF-R-alpha receptor is expressed preferentially in the cells of the tumour, whereas the PDGF-beta receptor is expressed preferentially in the vascular endothelial cells of the tumour. Blocking the kinase activity of PDGF-R has demonstrated its efficacy 1) in vitro by reducing the number of colonies on soft agar and inhibiting the proliferation of cell lines 2) on reduction of tumour growth in models of grafts in the nude mouse 3) in combination with irradiation in models of intracranial grafts of cells of glioblastoma lines (Oerbel et al., 2006; Geng et al., 2005, Strawn et al., 1994, Chin et al., 1997).

Thus, the compounds of the invention are of interest for Ewing sarcomas, GISTs, dermatofibrosarcomas but also desmoid tumours, haemangiomas and other fibrosarcomas for which data on expression of PDGF-R are available.

C. Targeting PDGF-R in the Tumour Environment

Angiogenesis

The cells in the environment around the tumour form an integral part of the development of cancer whether in the case of a primary tumour or secondary tumour (metastases). Among the cells in the environment that express PDGF-R and for which the role of this receptor has been demonstrated, we find the mural cells of vessels, i.e. pericytes and smooth muscle cells but also activated fibroblasts.

Angiogenesis is a process of generation of new capillary vessels from preexisting vessels or by mobilization and differentiation of bone marrow cells. Thus, both uncontrolled proliferation of endothelial cells and mobilization of angioblasts from bone marrow are observed in processes of neovascularization of tumours. It has been shown in vitro and in vivo that several growth factors stimulate endothelial proliferation such as VEGF and FGFs. In addition to these mechanisms, it has also been demonstrated that mural cells such as pericytes and smooth muscle cells contribute to stabilization of newly formed vessels. Invalidation of PDGF-R beta causes a deficit of pericytes in the mouse and leads to death of the animals at the end of gestation due to micro-haemorrhages and oedemas (Hellström et al., 1999, Hellström et al., 2001). In an elegant study of transplantation, expression of PDGF-R-beta by pericytes was shown to be necessary for their recruitment in tumour vessels by retention of PDGF-B by the endothelial cells but also by the PDGF-B secreted by the tumour cells (Abramsson et al., 2003). In the transgenic model Rip1Tag2 of pancreatic tumour, Song et al. also demonstrated expression of PDGF-R beta on the perivascular progenitors in the marrow derived from bone marrow, and these progenitors differentiate into mature pericytes around the tumour.

The advantage of blocking the activity of PDGF-R on the tumour pericytes was demonstrated by using the inhibitor of the tyrosine kinase activity of PDGF-R in animal models (transgenic model of tumour of the pancreas and implantation of glioma tumour), and the effect on tumour growth proves to be considerable in combination with an inhibitor of the kinase activity of VEGF-R (Bergers et al., 2003). Data in the literature (Cao et al., 2002, Fons et al., 2004) demonstrated the involvement of PDGF-R alpha and of PDGF-C in angiogenesis and in the differentiation of endothelial progenitors to cells such as pericytes and smooth muscle cells.

Activated Fibroblasts

PDGF-R is abundant in the tumoral stroma and is found on activated fibroblasts (myofibroblasts). It was shown in two studies that the combination of inhibitors or antagonists of PDGF-R with cytotoxic agents leads to a decrease in the microdensity of the vessels of ovarian cancers (Apte et al., 2004) and of pancreatic cancers (Hwang et al., 2003). PDGF-R beta regulates the pressure of the interstitial tissue of the tumour (Heuchel et al., 1999) and the co-administration of inhibitors of PDGF-R and chemotherapeutic agents improves their delivery into the tumour cells by reducing the intratumoral pressure (Griffon-Etienne, 1999). Finally in a murine model, administration of an inhibitor of the kinase activity of PDGF-R improves the consumption of chemotherapeutic agents by the tumour and thus increases their efficacy (Griffon-Etienne, 1999; Pietras et al., 2002; Pietras et al., 2003). These effects are most probably the effect of the TAFs (tumour-associated fibroblasts), also called CAFs (carcinoma-associated fibroblasts), activated fibroblasts present around the tumour which express PDGF-R, as illustrated by the recent works of Hwang et al., (2008), Kain et al. (2008), Pietras et al. (2008) in in-vivo models of pancreatic cancer and of cervical carcinogenesis. Stimulation by the PDGF ligand produced by the tumour cells stimulates the fibroblasts that produce the extracellular matrix and thus increase the interstitial tension. Furthermore, reducing this tension can facilitate delivery of drugs into the tumour and thus increase their efficacy. The activated fibroblasts present in the tumoral stroma therefore represent a novel therapeutic target in oncology (for review see Bouzin & Feron, 2007).

Metastases

Several works indicate that the PDGF-R and PDGF-ligand couple is involved in the development of metastases, probably by their action on angiogenesis and metastasization by the blood circulation, but also by a direct effect on lymphangiogenesis and therefore the metastases that are spread by the lymphatic vessels. A review notably documents the direct role of PDGF-BB in lymphangiogenesis and lymphatic metastases (Cao et al., 2005). However, most works implicate expression of PDGF-R in the environment of the metastases which promote the establishment and development of secondary tumours. The example most frequently reported is the development of bone metastases.

Example of Prostate Cancer:

Bone is frequently the site of metastases. 85 to 100% of patients who die from prostate cancer have bone metastases. Chemotherapy improves survival without progression and overall survival but because of the extreme heterogeneity of bone metastases in one and the same patient, chemotherapy does not provide a cure. It was shown using a model of immunodeficient mice that PDGF-BB plays an important role in the development of osteoblastic bone metastases in vivo (Yu et al., 2003). As for PDGF-DD, it speeds up the growth of prostate tumour cells and increases their interaction with the cells of the stroma. Expression of the PDGF alpha and beta receptor has been demonstrated respectively in 62 and 75% of prostate cancers. Moreover, an immunohistochemical study showed that the prostatic tumour and its metastases expressed PDGF-R (Hwang et al., 2003). Kim et al., (2003) showed that PDGF-R is expressed on bone metastases and on the vascular endothelial cells dependent on the metastases. An inhibitor of tyrosine kinase of PDGF-R combined with a cytotoxic agent substantially reduces bone metastases of prostate cancer in a murine model (Uehara et al., 2003). Moreover, this same combination leads to apoptosis of tumour cells, of vascular endothelial cells and inhibition of the growth of tumour cells in bone. Blocking of these receptors and of their signalling pathways in bone constitutes a novel therapeutic approach (Hwang et al., 2003; Uehara et al., 2003). In humans, clinical trials have shown the benefit offered by the combination of inhibitor of PDGF-R and of cytotoxic agent in patients with hormone-resistant prostate cancers with bone metastases. A decrease of the marker (prostate-specific antigen) PSA>50% was in fact observed in 38% of patients. The mean duration of PSA response was 8 months and the survival time without progression was 11 months.

Based on these various works, it appears that the compounds of the invention are of interest for the treatment of solid cancers by their effect on the surrounding cells, in combination with other therapeutic agents such as cytotoxic agents or inhibitors of angiogenesis.

D. Fibroses

Fibroses are often the cause of a primary event such as a cancer, treatment by radiotherapy, hepatitis, alcoholaemia. Involvement of PDGF is clearly demonstrated in pulmonary fibrosis (including asbestosis), renal fibrosis (glomerulonephritis), marrow fibrosis (often associated with megakaryocytic leukaemias), induced by radiotherapy as well as hepatic and pancreatic fibrosis (connected with alcoholaemia or with hepatitis) (for review see J C Bonner, 2004). Overexpression of PDGF was notably clearly shown, and results in in-vivo models with inhibitors of TK activity of PDGF-R have also been reported. Among these studies, that of Einter et al., (2002) showed that PDGF-CC is a potent inducer of renal fibrosis. The authors tested the efficacy of a neutralizing antibody in a model of unilateral urethral ligature, in which fibrosis develops particularly rapidly. They observed a very pronounced antifibrotic effect with a reduction in accumulation of myofibroblasts, a reduction in accumulation of extracellular matrix and a reduction in deposits of collagen IV. Another study conducted in a model of bleomycin-induced pulmonary fibrosis in the mouse showed the efficacy of an inhibitor of the TK activity of PDGF-R on prevention of fibrosis by inhibition of proliferation of mesenchymal cells (Aono et al., 2005). In a model of asbestos-induced fibrosis, an inhibitor of PDGF-R TK reduced the progression of fibrosis in the pulmonary parenchyma and the deposition of collagen (Vuorinen K, Gao F, Oury T D, Kinnula V L, Myllärniemi M. Imatinib mesylate inhibits fibrogenesis in asbestos-induced interstitial pneumonia. Exp Lung Res. 2007 September; 33(7):357-73). Several teams have demonstrated involvement of PDGF-R in hepatic fibrosis. It has been clearly demonstrated that PDGFBB and DD possess pro-fibrogenic characteristics on hepatic stellate cells (Rovida et al., 2008; Borkham-Kamphorst et al., 2007). In vivo, an inhibitor of PDGF-R TK is capable of reducing early fibrogenesis in a model of ligature of the biliary duct in the rat (Neef et al., 2006).

Thus, in view of the data in the literature, the compounds of the invention appear to be of therapeutic interest for various types of fibrosis.

E. Vascular Diseases: Atherosclerosis and Restenosis, Arteriosclerosis

The proliferation and migration of vascular smooth muscle cells contribute to intimal hypertrophy of the arteries and thus play a predominant role in atherosclerosis and in restenosis after angioplasty and endarterectomy. It was clearly demonstrated in vitro and in vivo in animal models that PDGF is involved in these phenomena. In vivo, it was notably shown that there is increased expression of PDGF in a vein graft model in the pig. Moreover, it was also shown that an inhibitor of the TK activity of PDGF-R consistently reduced the size of lesions of the thoracic and abdominal artery of ApoE-KO diabetic mice (animals treated with streptozotocin). Another study showed that inhibition of signalling induced by PDGF (TK or PDGF A antisense) leads to a decrease in neointima formation in "balloon injury" and "coronary artery restenosis" models. (Deguchi J, 1999, Ferns et al., 1991, Sirois et al., 1997, Lindner et al., 1995)

Thus, inhibitors of the tyrosine kinase activity of PDGF-R, such as the compounds of the present invention, represent a therapy of choice, either alone, or in combination with compounds that are antagonists of other growth factors involved in these pathologies such as FGF, in the treatment of pathologies connected with proliferation of vascular smooth muscle cells such as atherosclerosis, post-angioplasty restenosis or following placement of endovascular prostheses (stents) or during aorto-coronary bypasses.

By virtue of their inhibitory activity on the TK activity of PDGF-R, the compounds of the invention appear to be of interest for treating these vascular diseases.

F. Others

Other pathologies appear to be possible indications for the compounds of the invention, including idiopathic pulmonary arterial hypertension (PAH). PAH, characterized by a significant and sustained increase in pressure in the pulmonary artery, leads to right ventricular heart failure and often to patient death. It is associated with increase in the proliferation and migration of smooth muscle cells of the pulmonary vessels. Schermuly et al., (2005) showed that inhibition of the tyrosine kinase activity of the PDGF receptors greatly improves the progression of the disease. For this, among other things they used a model of experimental pulmonary arterial hypertension in the rat, obtained by administration of monocrotaline for 28 days. All the treated rats survived, whereas 50% of those in the untreated control group died.

The compounds of the invention might also be of therapeutic interest in pathologies of the eye. On the one hand, they might contribute to prevention of post-operative fibrosis in the case of cicatricial lesions of the cornea and of keratoconus. This could be explained by their action on proliferation of myofibroblasts as reported recently by Kaur et al., (2009). Moreover, they might also promote neovascular regression for pathologies such as ARMD (age-related macular degeneration). This was in fact demonstrated by several teams in experimental models, including notably Jo et al.; Dell et al., in 2006.

The present invention relates to derivatives of pyridinopyridinones substituted (i) in position 3 with an imidazole itself substituted with a group R1 and substituted (ii) in position 7 with an aryl or heteroaryl, itself substituted optimally with a motif of the type —[C(R3)(R4)]$_m$—CO—N(R5)(R6). The present invention also relates to the preparation of said compounds and application thereof in therapeutics as inhibitors of the kinase activity of receptors for PDGF (platelet derived growth factors) ligands and optionally of receptors for the FLT3 (fms-like tyrosine kinase receptor) ligand.

The present invention relates to compounds corresponding to formula (I):

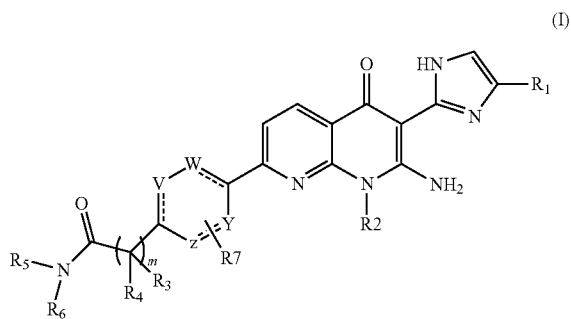

(I)

in which,

R1 represents a hydrogen atom or a ($C_1$-$C_4$)alkyl group;

R2 represents a group —($CH_2$)$_{n'}$—B where:

n'=0, 1, 2, 3 or 4; and

B represents (i) a ($C_3$-$C_5$)cycloalkyl group or a ($C_1$-$C_4$) alkyl group, said group being optionally substituted with one or more fluorine atoms, or (ii) a ($C_1$-$C_4$)alkoxy group;

Y, Z, V and W represent, independently of one another:

a —CH— group, a carbon atom optionally substituted with a group R7, said group R7 representing a ($C_1$-$C_4$)alkyl group or a halogen atom, a heteroatom such as a nitrogen atom, a sulphur atom or an oxygen atom, or no atom, it being understood that the ring in which V, W, Y and Z are comprised is a ring comprising 5 or 6 ring members, it being understood that the dotted lines in said ring indicate that the resultant ring is an aromatic ring and it being understood that said ring comprises 0, 1 or 2 heteroatoms;

R3 and R4 represent, independently of one another, groups that may be identical or different, R3 and R4 being selected from:

a hydrogen atom; and a linear ($C_1$-$C_4$)alkyl group;

or R3 and R4 form, together with the carbon to which they are bound, a ($C_3$-$C_5$) cycloalkyl group;

m is an integer equal to 1, 2, 3 or 4;

R5 represents a hydrogen atom or a ($C_1$-$C_4$)alkyl group;

R6 represents a group —($CH_2$)$_n$-L in which:

n=0, 1, 2 or 3, and

L is a group selected from the following groups:

an aryl comprising 6 carbon atoms;

a heteroaryl comprising between 5 and 6 ring members and comprising at least one heteroatom selected from nitrogen, oxygen and sulphur;

a saturated heterocycle comprising 5, 6 or 7 ring members and comprising at least one heteroatom selected from nitrogen and oxygen, said heterocycle being optionally a lactam;

said aryl, heteroaryl or heterocyclic group being optionally substituted with at least one substituent selected from (i) linear or branched ($C_1$-$C_4$)alkyl groups, (ii) ($C_3$-$C_5$)cycloalkyl groups, (iii) halogen atoms, (iv) aryls and (v) benzyl;

it being understood that when L is a heteroaryl or a heterocycle, said heteroaryl or heterocycle comprising at least one nitrogen atom, the latter can optionally be substituted with said substituent;

or R5 and R6 form, together with the nitrogen atom to which they are bound, a heterocyclic group, optionally substituted with at least a heteroaryl, or a ($C_1$-$C_3$)alkyl group, which can itself be substituted with a heterocycle comprising 5 or 6 atoms and comprising at least one heteroatom selected from nitrogen and oxygen, it being understood that when it is a heterocycle comprising at least one nitrogen atom, the latter can optionally be substituted;

said compound of formula (I), its enantiomers and diastereoisomers, including mixtures thereof, being in the form of a base or a salt of addition to an acid, for example such as trifluoroacetic acid (TFA) or hydrochloric acid and/or in the form of solvate.

The compounds of formula (I) can comprise one or more asymmetric carbon atoms. They can therefore exist in the form of enantiomers or of diastereoisomers. These enantiomers, diastereoisomers, as well as mixtures thereof, including racemic mixtures, form part of the invention. For example, when L represents a heterocycle, the absolute configuration of a carbon substituted on said heterocycle can be R or S, or when R3 is different from R4.

The compounds of formula (I) can exist in the form of bases or of salts of addition to an acid or to acids. Said salts of addition form part of the invention. These salts can be prepared with pharmaceutically acceptable acids, but salts of other acids that may be used for example for purification or isolation of the compounds of formula (I) also form part of the invention.

The compounds of formula (I) can also exist in the form of solvates, namely in the form of associations or of combinations with one or more molecules of solvent. Said solvates also form part of the invention.

Within the scope of the present invention, the following definitions are used:

alkyl group: a saturated aliphatic group comprising 1 to 7 carbon atoms (advantageously, a saturated aliphatic group comprising 1 to 4 carbon atoms and abbreviated to ($C_1$-$C_4$)alkyl) and being linear or, when the alkyl chain comprises at least 3 carbon atoms, possibly being branched or cyclic. As examples, we may mention methyl, ethyl, propyl, isopropyl, butyl, isobutyl, tert-butyl, methyl-cyclopropyl, pentyl, 2,2-dimethylpropyl, hexyl and heptyl groups, as well as the cycloalkyl groups defined below;

cycloalkyl group: a cyclic alkyl group comprising 3 to 7 carbon atoms (advantageously from 3 to 5 carbon atoms) and in which all the carbon atoms are inserted in the ring. We may mention the cyclopropyl, cyclobutyl, cyclopentyl, cyclohexyl and cycloheptyl groups;

alkoxy group: an —O-alkyl group, where the alkyl group is as defined above;

halogen atom: a fluorine, a chlorine, a bromine or an iodine atom;

haloalkyl group: a group comprising an alkyl group as defined above in which one or more hydrogen atoms have been substituted with one or more halogen atoms as defined above; thus, the term fluoroalkyl is used when the halogen in question is fluorine, heteroatom: a nitrogen, oxygen or sulphur atom;

aryl group: a monocyclic aromatic group comprising 6 ring members, for example a phenyl group;

heteroaryl group: a monocyclic aromatic group comprising between 5 and 7 ring members including between 1 and 3 heteroatoms as defined previously. As examples, we may mention the pyridine, pyrazine, pyrimidine, imidazole, pyrrole, pyrazole, thiophene, thiazole, isothiazole, thiadiazole, oxazole and isoxazole groups;

heterocyclic group: a cyclic alkyl group comprising between 5 and 7 ring members including one or more heteroatoms as defined previously. As examples, we may mention the pyrrolidine, morpholine, piperidine, piperazine and tetrahydrofuran groups.

The aforementioned groups can be substituted, knowing moreover that in the case of heteroaryl or heterocyclic groups comprising at least one nitrogen atom, substitution can take place on this nitrogen atom when such a substitution proves chemically possible.

Among the compounds of formula (I) according to the invention, we may mention compounds for which:
R5 represents a hydrogen atom or a methyl, or R5 and R6 form, together with the nitrogen atom to which they are bound, a heterocyclic group, optionally substituted with at least
a heteroaryl, advantageously a pyridine; or
a $(C_1-C_3)$alkyl group, which can itself be substituted with a heterocycle comprising 5 or 6 atoms and comprising at least one heteroatom selected from nitrogen and oxygen, advantageously it is a C1alkyl group, itself substituted with a heterocycle comprising 5 atoms including a nitrogen atom;
and/or
m is equal to 0, 1 or 3,
and/or
R3 and R4 represent, independently of one another, groups that may be identical or different, R3 and R4 being selected from:
a hydrogen atom, and
a methyl,
and/or
Y, Z, V and W represent, independently of one another:
a —CH— group;
a carbon atom substituted with a group R7, said group R7 representing a $(C_1-C_4)$alkyl group or a fluorine atom; or
a heteroatom such as a nitrogen atom, a sulphur atom or an oxygen atom, advantageously a nitrogen atom,
and/or
R1 represents a hydrogen atom or a methyl,
and/or
R2 represents a group —$(CH_2)_{n'}$—B where:
n'=0, 1 or 3; and/or
B represents (i) a $(C_3-C_5)$cycloalkyl group, (ii) a $(C_1-C_4)$alkyl group or (iii) a $(C_1-C_4)$alkoxy group,
and/or
the compounds of formula (I) in the form of a base or of a salt of addition to an acid such as hydrochloric acid or trifluoroacetic acid.

Among the compounds of formula (I) according to the invention, a first subgroup of compounds consists of compounds for which:
R6 represents a group —$(CH_2)_n$-L in which:
n=0, 1, 2 or 3, and
L is a group selected from the following groups:
a heteroaryl comprising 5 ring members and comprising (i) 2 heteroatoms selected, independently of one another, from nitrogen, oxygen and sulphur, or (ii) 3 heteroatoms selected, independently of one another, from nitrogen and sulphur,
a heteroaryl comprising 6 ring members and comprising 1 or 2 heteroatom(s),
a heterocycle comprising 5 ring members and comprising a heteroatom selected from nitrogen and oxygen, said heterocycle being optionally a lactam, and
a heterocycle comprising 6 ring members and comprising 2 heteroatoms selected from nitrogen and oxygen,
said heteroaryl group or heterocycle being optionally substituted with at least one substituent selected from (i) linear or branched $(C_1-C_4)$alkyl groups, (ii) $(C_3-C_5)$cycloalkyl groups, (iii) halogen atoms, (iv) aryls and (v) benzyl,
it being understood that when L is a heteroaryl or a heterocycle, said heteroaryl or heterocycle comprising at least one nitrogen atom, the latter can optionally be substituted with said substituent.

Among the compounds of formula (I) according to the invention, a second subgroup of compounds consists of compounds for which L is:
a heteroaryl comprising 6 ring members selected from pyridine, pyrazine, pyridazine and pyrimidine, or
an aryl such as phenyl, or
a heteroaryl comprising 5 ring members selected from thiazole, imidazole, pyrazole, isoxazole and 1,3,4-thiadiazole, or
a saturated heterocycle comprising 5 ring members selected from pyrrolidine, tetrahydrofuran and 2-oxo-pyrrolidine, or
a saturated heterocycle comprising 6 ring members selected from morpholine, piperazine and piperidine,
said aryl, heteroaryl or heterocyclic group being optionally substituted with at least one substituent selected from (i) linear or branched $(C_1-C_4)$alkyl groups, (ii) $(C_3-C_5)$cycloalkyl groups and (iii) aryls,
it being understood that when L is a heteroaryl or a heterocycle, said heteroaryl or heterocycle comprising at least one nitrogen atom, the latter can optionally be substituted with said substituent.

Among the compounds of formula (I) according to the invention, a third subgroup of compounds consists of compounds for which L is selected from:
pyridine, optionally substituted with at least one linear or branched $(C_1-C_4)$alkyl group,
morpholine, optionally substituted with at least (i) a $(C_3-C_5)$cycloalkyl group or (ii) a linear or branched $(C_1-C_4)$alkyl group,
a pyrrolidine, optionally substituted with at least (i) a linear or branched $(C_1-C_4)$alkyl group, or (ii) a benzyl,
a thiazole, optionally substituted with at least (i) a linear or branched $(C_1-C_4)$alkyl group, or (ii) a chlorine atom,
an imidazole, optionally substituted with at least one linear or branched $(C_1-C_4)$alkyl group,
a gamma-lactam,
a 1,3,4-thiadiazole, optionally substituted with at least (i) a linear or branched $(C_1-C_4)$alkyl group, or (ii) a $(C_3-C_5)$ cycloalkyl group,
an isoxazole, optionally substituted with at least one linear or branched $(C_1-C_4)$alkyl group,
a pyrazole, optionally substituted with at least one linear or branched $(C_1-C_4)$alkyl group,
a pyrazine,
an isothiazole, optionally substituted with at least one linear or branched $(C_1-C_4)$alkyl group,
a phenyl,
a tetrahydrofuran,
it being understood that when L is a heteroaryl or a heterocycle, said heteroaryl or heterocycle comprising at least one nitrogen atom, the latter can optionally be substituted.

Among the compounds of formula (I) according to the invention, we may notably mention the following compounds:

2-{-4-[7-Amino-8-ethyl-6-(1H-imidazol-2-yl)-5-oxo-5,8-dihydro-[1,8]naphthyridin-2-yl]-phenyl}-N-pyridin-2-yl-acetamide (compound 1)

2-{6-[7-Amino-8-ethyl-6-(1H-imidazol-2-yl)-5-oxo-5,8-dihydro-[1,8]naphthyridin-2-yl]-pyridin-3-yl}-N-pyridin-2-yl-acetamide (compound 2)

2-{4-[7-Amino-8-ethyl-6-(1H-imidazol-2-yl)-5-oxo-5,8-dihydro-[1,8]naphthyridin-2-yl]-phenyl}-N-(4-cyclopropyl-morpholin-3-ylmethyl)-acetamide (compound 3)

2-{4-[7-Amino-8-ethyl-6-(1H-imidazol-2-yl)-5-oxo-5,8-dihydro-[1,8]naphthyridin-2-yl]-phenyl}-N-(4-isopropyl-morpholin-3-ylmethyl)-acetamide (compound 4)

2-Amino-1-ethyl-3-(1H-imidazol-2-yl)-7-{4-[2-oxo-2-((S)-2-pyrrolidin-1-ylmethyl-pyrrolidin-1-yl)ethyl]-phenyl}-1H-[1,8]naphthyridin-4-one (compound 5)

2-{4-[7-Amino-8-ethyl-6-(1H-imidazol-2-yl)-5-oxo-5,8-dihydro-[1,8]naphthyridin-2-yl]-phenyl}-N-(2-pyridin-4-yl-ethyl)-acetamide (compound 6)

2-{4-[7-Amino-8-ethyl-6-(1H-imidazol-2-yl)-5-oxo-5,8-dihydro-[1,8]naphthyridin-2-yl]-phenyl}-N-methyl-N-(2-pyridin-4-yl-ethyl)-acetamide (compound 7)

2-{4-[7-Amino-8-ethyl-6-(1H-imidazol-2-yl)-5-oxo-5,8-dihydro-[1,8]naphthyridin-2-yl]-phenyl}-N-(5-methyl-thiazol-2-yl)-acetamide (compound 8)

2-{4-[7-Amino-8-ethyl-6-(1H-imidazol-2-yl)-5-oxo-5,8-dihydro-[1,8]naphthyridin-2-yl]-3-methyl-phenyl}-N-(1-ethyl-pyrrolidin-2-ylmethyl)-acetamide (compound 9)

2-{4-[7-Amino-8-ethyl-6-(1H-imidazol-2-yl)-5-oxo-5,8-dihydro-[1,8]naphthyridin-2-yl]-phenyl}-N-(6-methyl-pyridin-3-yl)-acetamide (compound 10)

2-{4-[7-Amino-8-ethyl-6-(1H-imidazol-2-yl)-5-oxo-5,8-dihydro-[1,8]naphthyridin-2-yl]-phenyl}-N-(1,3-dimethyl-1H-pyrazol-4-ylmethyl)-acetamide (compound 11)

2-{4-[7-Amino-8-ethyl-6-(1H-imidazol-2-yl)-5-oxo-5,8-dihydro-[1,8]naphthyridin-2-yl]-phenyl}-N-thiazol-2-ylmethyl-acetamide (compound 12)

2-{4-[7-Amino-8-ethyl-6-(1H-imidazol-2-yl)-5-oxo-5,8-dihydro-[1,8]naphthyridin-2-yl]-phenyl}-N-(5-oxo-pyrrolidin-2-ylmethyl)-acetamide (compound 13)

2-{4-[7-Amino-8-ethyl-6-(1H-imidazol-2-yl)-5-oxo-5,8-dihydro-[1,8]naphthyridin-2-yl]-phenyl}-N-(5-methyl-[1,3,4]thiadiazol-2-yl)-acetamide (compound 14)

2-{4-[7-Amino-8-ethyl-6-(1H-imidazol-2-yl)-5-oxo-5,8-dihydro-[1,8]naphthyridin-2-yl]-phenyl}-N-[1,3,4]thiadiazol-2-yl-acetamide (compound 15)

2-{4-[7-Amino-8-ethyl-6-(1H-imidazol-2-yl)-5-oxo-5,8-dihydro-[1,8]naphthyridin-2-yl]-phenyl}-N-(3-methyl-isoxazol-5-yl)-acetamide (compound 16)

2-{4-[7-Amino-8-ethyl-6-(1H-imidazol-2-yl)-5-oxo-5,8-dihydro-[1,8]naphthyridin-2-yl]-phenyl}-N-[2-(1-methyl-pyrrolidin-2-yl)-ethyl]-acetamide (compound 17)

2-{4-[7-Amino-8-ethyl-6-(1H-imidazol-2-yl)-5-oxo-5,8-dihydro-[1,8]naphthyridin-2-yl]-phenyl}-N-(4-methyl-thiazol-2-yl)-acetamide (compound 18)

2-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-acetamide (compound 19)

2-{4-[7-Amino-8-ethyl-6-(1H-imidazol-2-yl)-5-oxo-5,8-dihydro-[1,8]naphthyridin-2-yl]-phenyl}-N-(5-cyclopropyl-[1,3,4]thiadiazol-2-yl)-acetamide (compound 20)

2-{4-[7-Amino-8-ethyl-6-(1H-imidazol-2-yl)-5-oxo-5,8-dihydro-[1,8]naphthyridin-2-yl]-phenyl}-N-(2-pyridin-3-yl-ethyl)-acetamide (compound 21)

2-{4-[7-Amino-8-ethyl-6-(1H-imidazol-2-yl)-5-oxo-5,8-dihydro-[1,8]naphthyridin-2-yl]-phenyl}-N-(2,5-dimethyl-2H-pyrazol-3-ylmethyl)-acetamide (compound 22)

2-{4-[7-Amino-8-ethyl-6-(1H-imidazol-2-yl)-5-oxo-5,8-dihydro-[1,8]naphthyridin-2-yl]-phenyl}-N-(1-methyl-1H-imidazol-4-ylmethyl)-acetamide (compound 23)

2-{4-[7-Amino-8-ethyl-6-(1H-imidazol-2-yl)-5-oxo-5,8-dihydro-[1,8]naphthyridin-2-yl]-phenyl}-N-pyrazin-2-yl-acetamide (compound 24)

2-{4-[7-Amino-8-ethyl-6-(1H-imidazol-2-yl)-5-oxo-5,8-dihydro-[1,8]naphthyridin-2-yl]-phenyl}-N-(2-pyridin-2-yl-ethyl)-acetamide (compound 25)

2-{4-[7-Amino-8-ethyl-6-(1H-imidazol-2-yl)-5-oxo-5,8-dihydro-[1,8]naphthyridin-2-yl]-phenyl}-N-(5-chloro-thiazol-2-yl)-acetamide (compound 26)

2-{4-[7-Amino-8-ethyl-6-(1H-imidazol-2-yl)-5-oxo-5,8-dihydro-[1,8]naphthyridin-2-yl]-phenyl}-N-(3,4-dimethyl-isoxazol-5-yl)-acetamide (compound 27)

2-{4-[7-Amino-8-ethyl-6-(1H-imidazol-2-yl)-5-oxo-5,8-dihydro-[1,8]naphthyridin-2-yl]-phenyl}-N-(2-methyl-pyridin-4-yl)-acetamide (compound 28)

2-{4-[7-Amino-8-ethyl-6-(1H-imidazol-2-yl)-5-oxo-5,8-dihydro-[1,8]naphthyridin-2-yl]-phenyl}-N-pyrazin-2-ylmethyl-acetamide (compound 29)

2-{4-[7-Amino-8-ethyl-6-(1H-imidazol-2-yl)-5-oxo-5,8-dihydro-[1,8]naphthyridin-2-yl]-phenyl}-N-(5-ethyl-[1,3,4]thiadiazol-2-yl)-acetamide (compound 30)

2-{4-[7-Amino-8-ethyl-6-(1H-imidazol-2-yl)-5-oxo-5,8-dihydro-[1,8]naphthyridin-2-yl]-phenyl}-N-(tetrahydro-furan-2-ylmethyl)-acetamide (compound 31)

2-{4-[7-Amino-8-ethyl-6-(1H-imidazol-2-yl)-5-oxo-5,8-dihydro-[1,8]naphthyridin-2-yl]-phenyl}-N-(3-methyl-pyridin-2-yl)-acetamide (compound 32)

2-{4-[7-Amino-8-ethyl-6-(1H-imidazol-2-yl)-5-oxo-5,8-dihydro-[1,8]naphthyridin-2-yl]-phenyl}-N-(4-methyl-pyridin-2-yl)-acetamide (compound 33)

2-{4-[7-Amino-8-ethyl-6-(1H-imidazol-2-yl)-5-oxo-5,8-dihydro-[1,8]naphthyridin-2-yl]-phenyl}-N-(4,6-dimethyl-pyridin-2-yl)-acetamide (compound 34)

2-{4-[7-Amino-8-ethyl-6-(1H-imidazol-2-yl)-5-oxo-5,8-dihydro-[1,8]naphthyridin-2-yl]-phenyl}-N-(6-methyl-pyridin-2-yl)-acetamide (compound 35)

2-{4-[7-Amino-8-ethyl-6-(1H-imidazol-2-yl)-5-oxo-5,8-dihydro-[1,8]naphthyridin-2-yl]-phenyl}-N-pyridin-3-ylmethyl-acetamide (compound 36)

2-{4-[7-Amino-8-ethyl-6-(1H-imidazol-2-yl)-5-oxo-5,8-dihydro-[1,8]naphthyridin-2-yl]-phenyl}-N-(2-ethyl-2H-pyrazol-3-yl)-acetamide (compound 37)

2-{4-[7-Amino-8-ethyl-6-(1H-imidazol-2-yl)-5-oxo-5,8-dihydro-[1,8]naphthyridin-2-yl]-phenyl}-N-(3-methyl-isothiazol-5-yl)-acetamide (compound 38)

2-Amino-1-ethyl-3-(1H-imidazol-2-yl)-7-{4-[2-oxo-2-(2-pyridin-3-yl-pyrrolidin-1-yl)-ethyl]-phenyl}-1H-[1,8]naphthyridin-4-one (compound 39)

2-{4-[7-Amino-8-ethyl-6-(1H-imidazol-2-yl)-5-oxo-5,8-dihydro-[1,8]naphthyridin-2-yl]-phenyl}-N-(1-benzyl-pyrrolidin-3-yl)-acetamide (compound 40)

2-{4-[7-Amino-8-ethyl-6-(1H-imidazol-2-yl)-5-oxo-5,8-dihydro-[1,8]naphthyridin-2-yl]-phenyl}-N—[(S)-1-(tetrahydro-furan-2-yl)methyl]-acetamide (compound 41)

2-{4-[7-Amino-8-ethyl-6-(1H-imidazol-2-yl)-5-oxo-5,8-dihydro-[1,8]naphthyridin-2-yl]-phenyl}-N-(4-methyl-pyridin-3-yl)-acetamide (compound 42)

2-{4-[7-Amino-8-ethyl-6-(1H-imidazol-2-yl)-5-oxo-5,8-dihydro-[1,8]naphthyridin-2-yl]-phenyl}-N-(4-ethyl-pyridin-2-yl)-acetamide (compound 43)

2-{4-[7-Amino-8-ethyl-6-(1H-imidazol-2-yl)-5-oxo-5,8-dihydro-[1,8]naphthyridin-2-yl]-phenyl}-N-ethyl-N-pyridin-4-ylmethyl-acetamide (compound 44)

2-{4-[7-Amino-8-ethyl-6-(1H-imidazol-2-yl)-5-oxo-5,8-dihydro-[1,8]naphthyridin-2-yl]-phenyl}-N-(6-ethyl-pyridin-2-yl)-acetamide (compound 45)

2-{4-[7-Amino-8-ethyl-6-(1H-imidazol-2-yl)-5-oxo-5,8-dihydro-[1,8]naphthyridin-2-yl]-phenyl}-N-benzyl-acetamide (compound 46)

2-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-propionamide (compound 47)

4-[7-Amino-8-ethyl-6-(1H-imidazol-2-yl)-5-oxo-5,8-dihydro-[1,8]naphthyridin-2-yl]-N-pyridin-4-ylmethyl-benzamide (compound 48)

4-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-butyramide (compound 49)

2-{4-[7-Amino-8-ethyl-6-(4-methyl-1H-imidazol-2-yl)-5-oxo-5,8-dihydro-[1,8]naphthyridin-2-yl]-phenyl}-N-pyridin-4-ylmethyl-acetamide (compound 50)

2-{4-[7-Amino-8-cyclopropylmethyl-6-(1H-imidazol-2-yl)-5-oxo-5,8-dihydro-[1,8]naphthyridin-2-yl]-phenyl}-N-pyridin-4-ylmethyl-acetamide (compound 51)

2-{4-[7-Amino-8-cyclopentyl-6-(1H-imidazol-2-yl)-5-oxo-5,8-dihydro-[1,8]naphthyridin-2-yl]-phenyl}-N-pyridin-4-ylmethyl-acetamide (compound 52)

2-{5-[7-Amino-8-ethyl-6-(1H-imidazol-2-yl)-5-oxo-5,8-dihydro-[1,8]naphthyridin-2-yl]-pyridin-2-yl}-N-pyridin-4-ylmethyl-acetamide (compound 53)

2-{4-[7-Amino-6-(1H-imidazol-2-yl)-8-(3-methoxy-propyl)-5-oxo-5,8-dihydro-[1,8]naphthyridin-2-yl]-phenyl}-N-pyridin-4-ylmethyl-acetamide (compound 54)

2-{4-[7-Amino-8-ethyl-6-(1H-imidazol-2-yl)-5-oxo-5,8-dihydro-[1,8]naphthyridin-2-yl]-phenyl}-N-(3-phenyl-propyl)-acetamide (compound 55)

2-{4-[7-Amino-8-ethyl-6-(1H-imidazol-2-yl)-5-oxo-5,8-dihydro-[1,8]naphthyridin-2-yl]-2-fluoro-phenyl}-N-(1-ethyl-pyrrolidin-2-ylmethyl)-acetamide (compound 56)

It should be noted that the above compounds were named in IUPAC nomenclature using the Autonom software.

Hereinafter, protecting group, denoted by Pg, means a group that makes it possible, on the one hand, to protect a reactive function such as a hydroxy or an amine during a synthesis and, on the other hand, to regenerate the intact reactive function at the end of synthesis. Examples of protecting groups as well as methods of protection and deprotection are given, for example, in "Protective Groups in Organic Synthesis", Green et al., $2^{nd}$ Edition (John Wiley & Sons, Inc., New York), 1991.

Leaving group means, hereinafter, a group that can be easily cleaved from a molecule by rupture of a heterolytic bond, with departure of an electron pair. This group can thus be replaced easily with another group during a substitution reaction, for example. Said leaving groups are, for example, halogens or an activated hydroxyl group such as a methanesulphonate, benzenesulphonate, p-toluenesulphonate, triflate, acetate, etc. Examples of leaving groups as well as references for their preparation are given in "Advances in Organic Chemistry", J. March, $3^{rd}$ Edition, Wiley Interscience, 1985, p. 310-316.

According to the invention, the compounds of general formula (I) can be prepared according to the method described in the following schemes 1, 2 and 3.

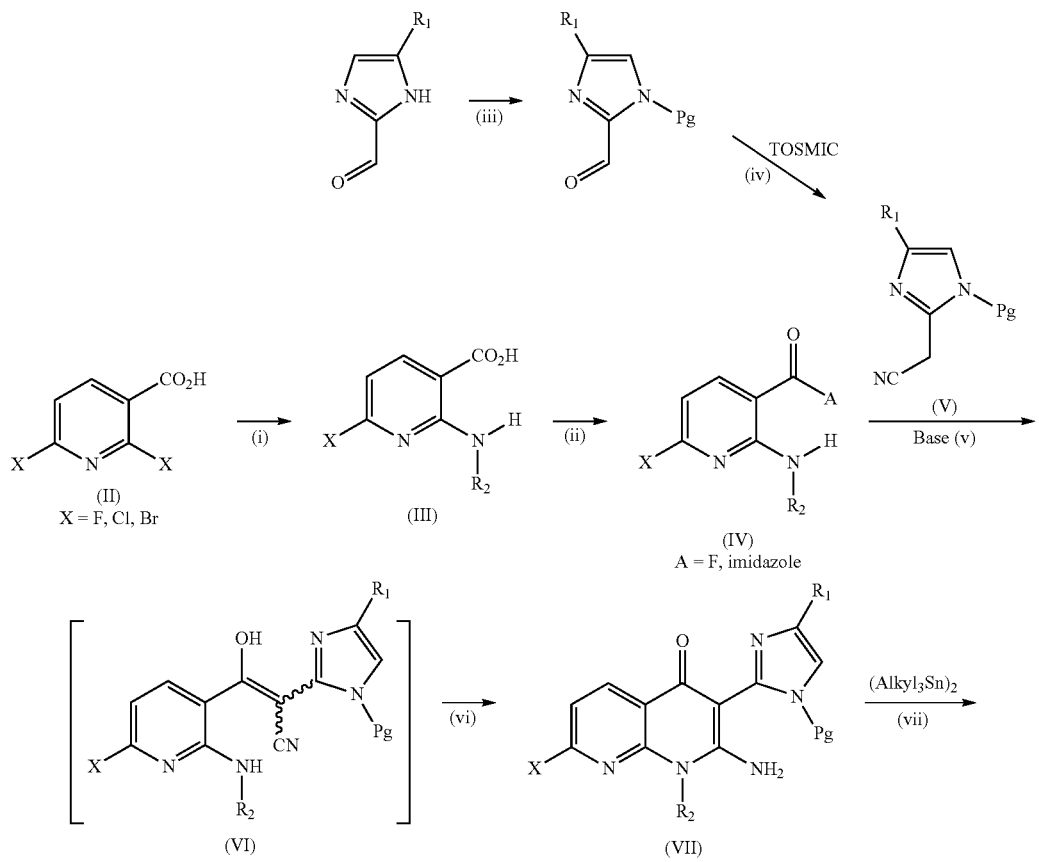

Scheme 1

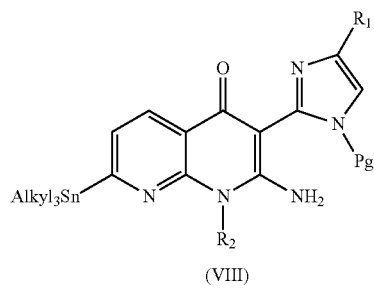

(VIII)

According to scheme 1, in stage (i), a 2,6-dihalogeno-nicotinic acid of formula (II) is mono-substituted in position 2 with an amine of formula R—$NH_2$ (where $R_2$ is as defined previously with reference to the compounds of formula (I)), at room temperature, or at a temperature from 50° C. to 100° C., with conventional heating or microwave heating and in a protic solvent such as an alcohol, for example ethanol, n-butanol, tert-butanol or water. The acid (III), resulting from stage (i), is then activated to a derivative of formula (IV), following stage (ii) either in the form of acid fluoride by the action of cyanuryl fluoride at room temperature, in the presence of a base such as triethylamine or pyridine and in an aprotic solvent such as dichloromethane or THF, as described by G. OLAH et al., in *Synthesis* (1973), 487, or in the form of imidazolide by the action of carbodiimidazole in a polar aprotic solvent such as DMF or THF or by other methods known by a person skilled in the art, such as those described by MUKAIYAMA and TANAKA in *Chem. Lett.* (1976), 303 or by ISHIKAWA and SASAKI in *Chem. Lett.* (1976), 1407.

The cyanoacetylimidazoles of formula (V) are prepared in two stages from an imidazole-2-carboxaldehyde unsubstituted or substituted in position (4,5) of the imidazole. In stage (iii) the free nitrogen of the imidazole-2-carboxaldehyde is protected by a protecting group, designated Pg in scheme 1, for example such as a SEM, Boc or trityl group, in conventional working conditions known by a person skilled in the art "Protective Groups in Organic Synthesis", Green et al., $2^{nd}$ Edition (John Wiley & Sons, Inc., New York). If applicable, the two isomers τ and π of the protected imidazole are obtained and used without distinction in the subsequent reactions. The protected imidazole-2-carboxaldehyde is then transformed in stage (iv) to cyanoacetylimidazole of formula (V) by reaction of the aldehyde function with the anion of TOSMIC, formed by adding potassium tert-butylate to anhydrous DME at low temperature (−50° C.), followed by ring opening of the anionic intermediate formed, 4-tosyl-2-oxazoline, then the reaction mixture is heated under reflux in the presence of methanol to permit formation of the acetylnitrile function following the method described by Van Leusen A. et al. (*Synthetic Comm,* 10(5) 1980, 399-403).

The acid fluoride or the imidazolide of formula (IV) obtained at the end of stage (ii), very reactive but stable, is then reacted, in stage (v), with a cyanoacetylimidazole of formula (V), unsubstituted or substituted in position (4,5), in the presence of one equivalent of a base such as sodium hydride or potassium tert-butoxide, in a polar aprotic solvent such as THF or DMF, at a temperature from −5° C. to room temperature, then a second equivalent of the base used is added and the compound of formula (VI) that formed is cyclized in situ, at room temperature, to give the pyridino-pyridinone compound of formula (VII), following stage (vi).

The halogenated intermediate of formula (VII) can then be transformed to the pyridino[2,3-b]pyridinone-7-stannous derivative of formula (VIII), by reacting it, in stage (vii), with a hexaalkyldistannous compound, where the alkyl can be either a butyl or a methyl, in the presence of a complex of palladium (in oxidation state (0) or (II)) for example such as $Pd(PPh_3)_4$, $PdCl_2(PPh_3)_2$, and optionally with addition of a ligand such as triphenyl arsine, trifurylphosphine in a polar or nonpolar solvent such as dioxane, THF, DMF or a nonpolar solvent such as toluene at a temperature between 50 and 110° C. according to the methodology described by Stille J K et al., (*JACS,* 1987, 109, 813).

To obtain the compounds of formula (I) according to the present invention, two methods can be used starting from the halogenated intermediate of formula (VII), according to method 1 described in scheme 2, or starting from the stannous compound of formula (VIII), according to method 2 described in scheme 3.

Scheme 2

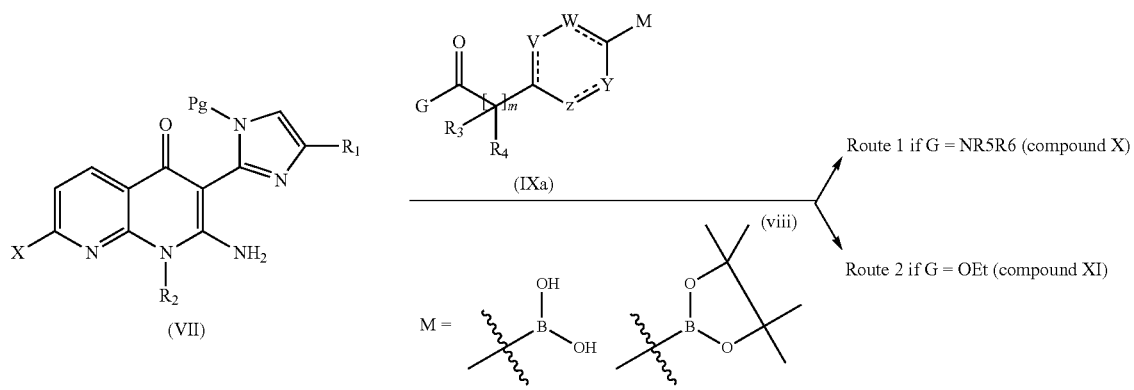

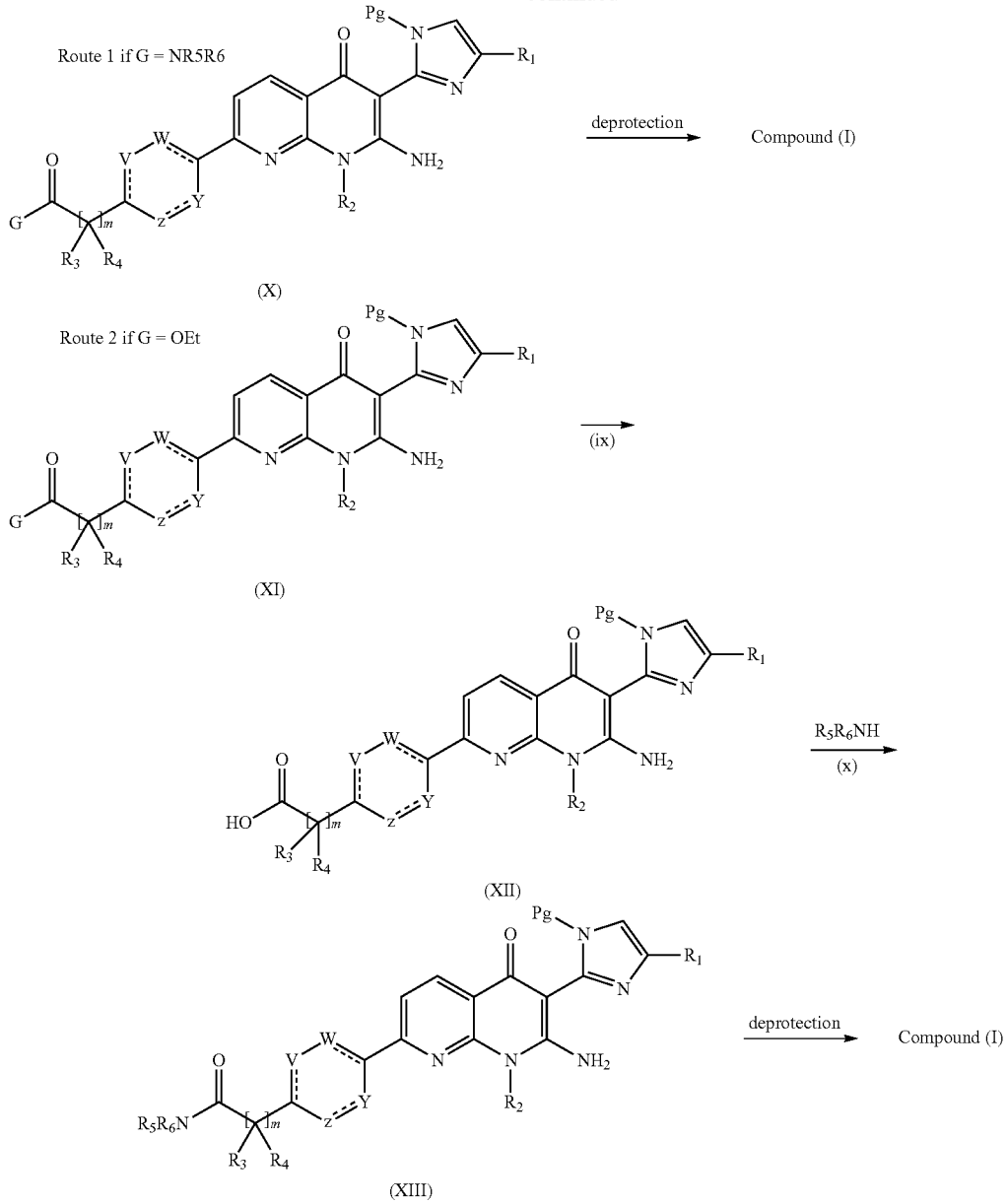

Following method 1 described in scheme 2, the intermediate (VII) is used in stage (viii) in a Suzuki coupling reaction with a boronic acid [formula (IXa) with M=—B(OH)$_2$] or a boronic ester of pinacol [formula (IXa) with Pg being a protecting group as defined previously, M=B(OC(CH$_3$)$_2$)$_2$] where m, R1, R2, R3, R4, V, W, Y and Z are as defined previously with reference to the compounds of formula (I) according to the invention, it being understood that the ring must comprise between 5 and 6 ring members, and G is either a (C$_1$-C$_4$)alkoxy group such as OEt or a motif-NR5R6, where R5 and R6 are as defined for the compound of formula (I). These compounds (IXa) are either commercial or are prepared from the corresponding halogenated derivatives according to the method of Miyaura et al. (*Chem Rev* 1995, 95, 2457).

This reaction (viii) is carried out in the presence of a complex of palladium (in oxidation state (0) or (II)) for example such as Pd(PPh$_3$)$_4$, PdCl$_2$(PPh$_3$)$_2$, Pd$_2$ dba$_3$, Xphos or PdCl$_2$ (dppf), in a protic or aprotic polar solvent such as DME, ethanol, DMF, dioxane, or mixtures of these solvents, in the presence of a base such as caesium carbonate, aqueous sodium hydrogen carbonate, or K$_3$PO$_4$, heating conventionally between 80 and 120° C. or by microwave heating between 130 and 170° C.

In the case when G is a motif NR5R6, where R5 and R6 are as defined for the compound of formula (I), it is route 1 that is followed, leading to compound (X), which after a conventional stage of deprotection, for example in the presence of an acid such as HCl (4N) in dioxane or trifluoroacetic acid in a solvent such as ethanol or dichloromethane, at a temperature between −5° C. and 60° C., gives the compound of formula (I) according to the invention.

In the case when G is a (C$_1$-C$_4$)alkoxy group such as OEt, it is route 2 that is followed, the compound (XI), obtained by Suzuki coupling in stage (viii), is saponified in stage (ix) in the presence of LiOH or NaOH, in a mixture of protic solvent such as water, methanol or ethanol and of aprotic solvent such as THF or DMF, at room temperature or by heating to a temperature between 50 and 100° C., to give compound (XII). The latter is then used in a peptide coupling reaction with the amine HNR5R6, where R5 and R6 are as defined for the compound of formula (I), in stage (x), in the presence of a coupling agent such as BTUT, BTUH or CDI and a base, for example diisopropylethylamine or NaHCO3, in an aprotic solvent such as dichloromethane, THF or DMF or by other methods known by a person skilled in the art, such as those described in "Principles of Peptide Synthesis", $2^{nd}$ Ed 1993 M Bodanszky, Springer Laboratory, to give the compound of formula (XIII), which after a conventional stage of deprotection, as described previously, gives the compound of formula (I) according to the invention.

According to method 2 described in scheme 3, compound (VIII) is used in a Stille coupling reaction with a halogenated derivative of formula (IXb) where Pg, m, R1, R2, R3, R4, V, W, Y and Z are as defined previously with reference to the compounds of formula (I) according to the invention, it being understood that the ring must comprise between 5 and 6 ring members, X is a halogen atom and G is either a ($C_1$-$C_4$)alkoxy group such as OEt or a motif —NR5R6, where R5 and R6 are as defined for the compound of formula (I). This reaction (xi) is carried out in the presence of a complex of palladium (in oxidation state (0) or (II)) for example such as Pd(PPh$_3$)$_4$, PdCl$_2$(PPh$_3$)$_2$ or Pd$_2$(dba)$_3$ and optionally with addition of a ligand such as triphenyl arsine, trifurylphosphine or triphenylphosphine in a polar aprotic solvent such as DMF, dioxane or THF with heating to a temperature between 50 and 120° C.

In the case when group G, on compound (IXb), is a motif NR5R6, where R5 and R6 are as defined for the compound of formula (I), it is route 1 that leads to formation of compound (X), which after a conventional stage of deprotection, as described previously, gives the compound of formula (I) according to the invention.

In the case when G is a ($C_1$-$C_4$)alkoxy group such as OEt, it is route 2 that is followed, and compound (XI) is obtained by the Stille coupling of stage (xi), and the subsequent stages, (xii), (xiii) and of deprotection to give respectively the compounds of formula (XII) and (XIII) and (I) according to the invention, are identical respectively to stages (ix), (x) and of deprotection described previously.

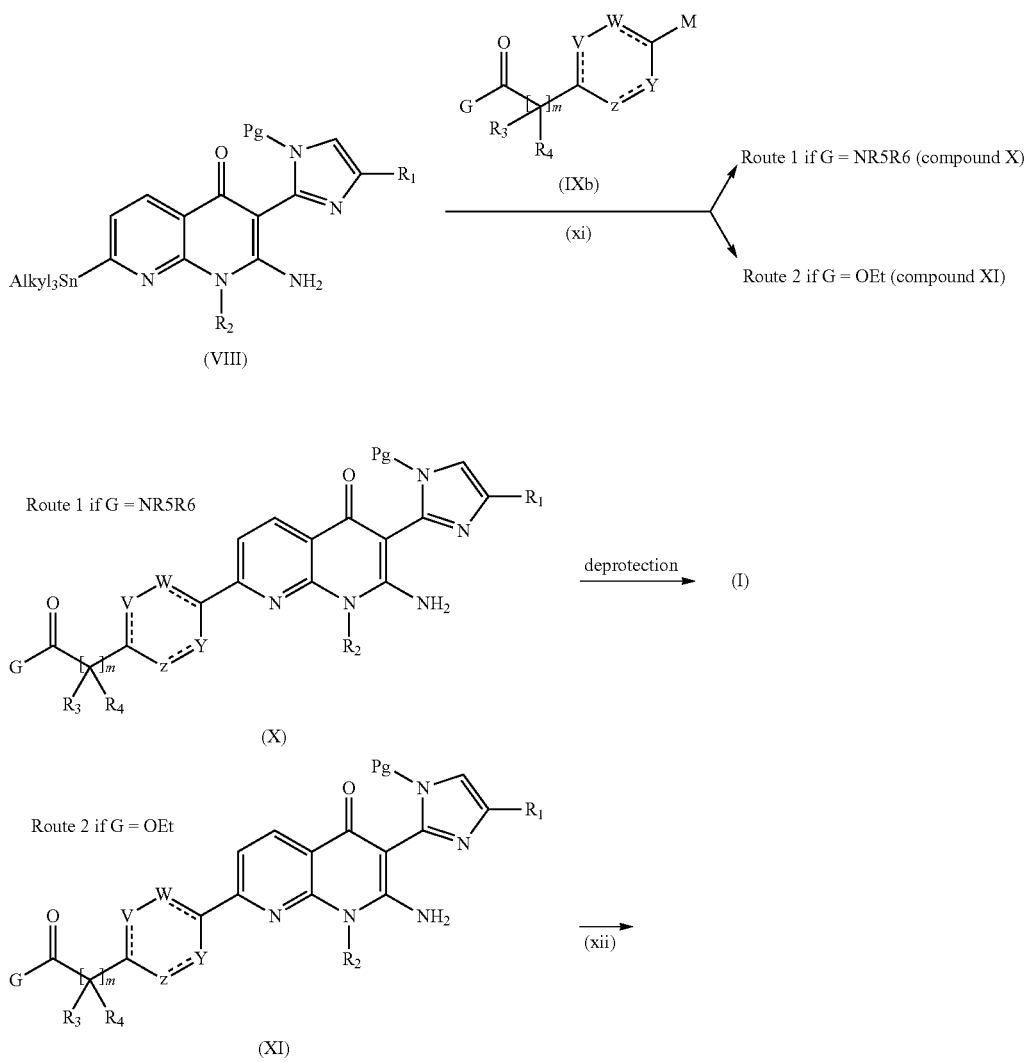

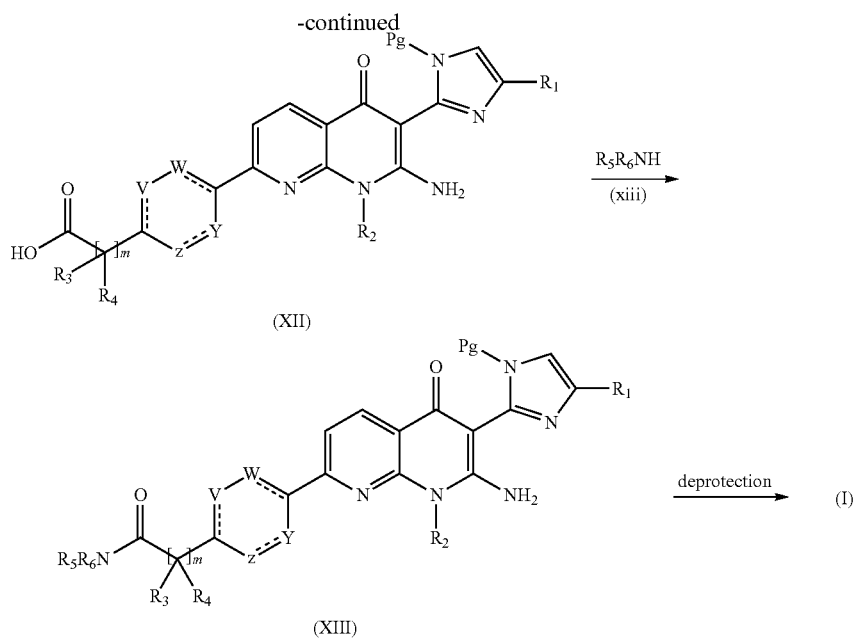

(XII)

(XIII)

If necessary, certain reactive functions located on group R5, R6, R7 or R2 can be protected in the course of these couplings by protecting groups, as described in "Protective Groups in Organic Synthesis", Green et al., 2$^{nd}$ Edition.

In schemes 1, 2, 3, the starting compounds and the reagents, when their manner of preparation is not described, are commercially available or are described in the literature, or else can be prepared according to methods that are described in the literature or that are known by a person skilled in the art.

According to another of its aspects, the invention also relates to the compounds of formulae (VII), (VIII), (XI). These compounds are useful as synthesis intermediates of the compounds of formula (I).

EXAMPLES

The following examples illustrate the preparation of certain compounds according to the invention. These examples are not limiting and their only purpose is to illustrate the present invention. The numbers of the compounds in the examples refer to those given in the following table, which presents the chemical structures and physical properties of some compounds according to the invention.

The following abbreviations and empirical formulae are used:

| | |
|---|---|
| EtOAc | Ethyl acetate |
| CDI | Carbonyldiimidazole |
| DCM | Dichloromethane |
| ° C. | degree Celsius |
| DME | Dimethoxyethane |
| DMF | Dimethylformamide |
| DMSO | Dimethyl sulphoxide |
| EDC•HCl | N-[3-(dimethylamino)propyl-N'-ethyl carbodiimide hydrochloride |
| BTUH | O-(-benzotriazol-1-yl)-N,N,N',N'-tetramethyluronium hexafluorophosphate. |
| h | Hour(s) |
| HCl | Hydrochloric acid |
| LiOH | Lithium hydroxide |
| $Na_2CO_3$ | Sodium carbonate |
| $NH_4Cl$ | Ammonium chloride |
| $NaHCO_3$ | Sodium hydrogen carbonate |
| $Na_2SO_4$ | Sodium sulphate |
| NaCl | Sodium chloride |
| NaOH | Sodium hydroxide |
| $NH_4OH$ | Ammonium hydroxide |
| $Na_2SO_4$ | Sodium sulphate |
| min. | minutes |
| ml | milliliter |
| $P_2O_5$ | diphosphorus pentoxide |
| SEM | 2-Trimethylsilanyl-ethoxymethyl |
| BTUT | N-[(1H-benzotriazol-1-yloxy)(dimethylamino)methylidene]-N-methylmethanaminium tetrafluoroborate |
| TFA | Trifluoroacetic acid |
| THF | Tetrahydrofuran |
| RT | Room temperature |
| Tr | retention time |
| TOSMIC | Toulenesulphonylmethyl isocyanide |
| Xphos | 2-Dicyclohexylphosphinol-2',4',6'-triisopropylbiphenyl |

Equipment Used:
Microwave Apparatus: Biotage, Initiator
Analysis Conditions:
LC/UV/MS Coupling Conditions:
Instrument (Agilent): HPLC chain: Series 1100, Mass spectrometer MSD SL (Agilent), Software: Chemstation version B.01.03 from Agilent
LC/UV
Column: Symmetry C18 3.5 µm (2.1×50 mm) (Waters), Column temp.: 25° C.,
Post run: 5 min UV Detection: 220 nm. Injection volume: 2 µl of a solution at 0.5 mg/ml
Condition 1: pH 3 gradient 15 minutes
Eluents: A: $H_2O$+0.005% TFA/B: $CH_3CN$+0.005% TFA, Flow: 0.4 ml/min. Gradient: 0 to 10 min 0 to 100% B and from 10 to 15 min 100 B %
Condition 2: pH 3 gradient 30 minutes
Column: Symmetry C18 3.5 µm (2.1×50 mm) (Waters), Column temp.: 25° C., Eluents:

A: H$_2$O+0.005% TFA/B: CH$_3$CN+0.005% TFA, Flow: 0.4 ml/min. Gradient: 0 to 30 min 0 to 100% B and from 30 to 35 min 100 B %

Post run: 6 min. UV Detection: 220 nm. Injection volume: 2 µl of a solution at 0.5 mg/ml Condition 3: pH 7 gradient 20 minutes
Column: X terra MS C18 3.5 µm (2.1×50 mm), Column temp.: 20° C. Eluents: A H$_2$O+AcNH$_4$ (5 nM)+3% CH$_3$CN/B: CH$_3$CN. Gradient 0 to 20 min 0 to 100% of B. UV Detection: 210 nm.

Condition GC Cl/CH$_4$+): ionization Cl/CH$_4$+, 30 minutes
Column: Agilent HP-5MS 30 m×250 µm film 0.25 µm thick. Temperature 250° C., Carrier gas: Helium, constant flow 1.4 ml/min MS:
ionization mode: Electrospray positive mode ESI+, mass range: 90-1500 uma Spray Chamber Gas temp.: 350° C. Drying gas (N$_2$): 10.0 l/min Neb. pressure: 30 psig Vcap: 4000 V The $^1$H NMR spectra were obtained using NMR spectrometers Bruker 250, 300 or 400 MHz in DMSO-d6, using the peak of DMSO-d5 as reference. The chemical shifts δ are expressed in parts per million (ppm). The signals observed are expressed as follows: s=singlet; d=doublet; t=triplet; m=multiplet or large singlet; H=proton.

The melting points below 260° C. were measured with a Kofler bench and melting points above 260° C. were measured with a Buchi B-545 instrument.

The rotating powers were measured on a polarimeter of the type: Polarimeter Perkin-Elmer, energy 55 µA.

Example 1

2-{6-[7-Amino-8-ethyl-6-(1H-imidazol-2-yl)-5-oxo-5,8-dihydro-[1,8]naphthyridin-2-yl]-pyridin-3-yl}-N-pyridin-2-yl-acetamide (compound 2)

1.1/6-Chloro-2-(ethylamino)pyridine-3-carboxylic acid

A solution of 18.0 g (84.4 mmol) of 2,6-dichloronicotinic acid in 180 ml (3.45 mol) of a 70% solution of ethylamine in water is heated at 50° C. for 10 hours. The excess amine is then evaporated under reduced pressure, then a 10% aqueous solution of acetic acid is added until the product is precipitated. The beige solid is filtered, rinsed with cold water and stove-dried. 10.5 g of the expected product is obtained. Yield=62%. Melting point: 158-160° C. MH$^+$: 201.1 (Tr: 7.7 min, condition 1).

1.2/6-Chloro-2-(ethylamino)pyridine-3-carboxylic fluoride 4.2 ml (52.3 mmol) of pyridine and 8.4 ml (99.6 mmol) of cyanuric fluoride are added successively to a suspension of 10.5 g (52.3 mmol) of the compound obtained at the end of stage 1.1 in dichloromethane (250 ml). The mixture is stirred for 3 hours at room temperature and then filtered. The solid is rinsed with dichloromethane (100 ml) and the filtrate is washed twice with ice water (60 ml). The organic phase is dried over Na$_2$SO$_4$ and then concentrated under reduced pressure. 10.44 g of product is obtained, in the form of an orange oil. Yield=99%. The product is used without purification in the next stage.

1.3/[1-(2-Trimethylsilanyl-ethoxymethyl)-1H-imidazol-2-yl]-acetonitrile

Under inert atmosphere, 0.91 g (4.6 mmol) of TOSMIC in solution in anhydrous DME (4 ml) is added to 0.96 g (8.6 mmol) of potassium tert-butylate in suspension in 4 ml of anhydrous DME at −35° C. The reaction mixture is cooled to −50° C. then 1 g (4.4 mmol) of 1-(2-trimethylsilanyl-ethoxymethyl)-1H-imidazole-2-carbaldehyde (Whitten J P, JOC 1986, 51 (10) 1891-1894) in solution in 4 ml of anhydrous DME is added dropwise, keeping the temperature below −45° C. The reaction mixture is stirred at this temperature for 30 min, then 11 ml of methanol is added, and the mixture is heated at 80° C. for 15 minutes. The solvents are concentrated under reduced pressure, and the residue is taken up in a water/acetic acid mixture (13 ml/0.5 ml), the aqueous phase is extracted with dichloromethane (3×100 ml), the organic phases are then washed with a saturated solution of NaHCO$_3$, then dried over Na$_2$SO$_4$. After filtration, the filtrate is concentrated under reduced pressure and the residue is purified by filtration on basic alumina (eluent: A/B=DCM/AcEt 0 to 50% of B), 0.71 g of compound is thus obtained in the form of a yellowish orange oil. Yield=67%. MH$^+$: 238 (Tr: 6.9 min, condition 1).

$^1$H NMR (300 MHz, DMSO-d$_6$), δ (ppm): 7.31 (d, 1H); 6.89 (d, 1H); 5.34 (s, 2H); 4.19 (s, 2H); 3.46 (dd, 2H); 0.87 (dd, 2H); 0 (s, 9H).

1.4/2-Amino-7-chloro-1-ethyl-3-[1-(2-trimethylsilanyl-ethoxymethyl)-1H-imidazol-2-yl]-1H-[1,8]naphthyridin-4-one Under inert atmosphere, 2.4 g (20.5 mmol) of potassium tert-butylate is added in portions to 4.9 g (20.5 mmol) of the compound obtained at the end of stage 1.3, in solution in anhydrous THF (50 ml) cooled to 0° C. After 45 minutes of stirring at room temperature, the reaction mixture is cooled to 0° C., and 4.2 g (20.5 mmol) of the compound obtained at the end of stage 1.2, in solution in anhydrous THF (20 ml), is added dropwise. The mixture is stirred at room temperature for one hour, then 3.5 g (30.8 mmol) of potassium tert-butylate is added and it is stirred for a further 2 hours. 500 ml of a saturated solution of ammonium chloride is added, and the medium is acidified to pH=4 by adding a solution (1N) of HCl. The aqueous phase is extracted with ethyl acetate (2×500 ml). The organic phases are washed with a saturated solution of sodium chloride, dried over Na$_2$SO$_4$, filtered and concentrated under reduced pressure. The residue is purified by silica gel flash chromatography (eluent: A/B=DCM/Methanol, from 0 to 5% of B). 6.1 g of compound is thus obtained in the form of a brown solid. Yield=70%. Melting point=90° C. MH$^+$: 419 (Tr: 6.6 min, condition 1).

$^1$H NMR (300 MHz, DMSO-d$_6$), δ (ppm): 8.47 (d, 1H); 7.67 (s, 2H); 7.44 (d, 1H); 7.33 (d, 1H); 7.1 (d, 1H); 5.27 (s, 2H); 4.45 (q, 2H); 3.22 (dd, 2H); 1.28 (t, 3H); 0.63 (dd, 2H); −0.2 (s, 9H).

1.5/2-Amino-1-ethyl-3-[1-(2-trimethylsilanyl-ethoxymethyl)-1H-imidazol-2-yl]-7-trimethylstannanol-1-1H-[1,8]naphthyridin-4-one In a sealed tube, a solution of 2 g of the compound obtained at the end of stage 1.4 in 12 ml of dioxane is degassed with argon for 15 minutes, then 2.05 g (6.2 mmol) of hexamethylditin, 0.16 g (0.50 mmol) of triphenylarsine and 0.54 g (0.75 mmol) of bis(triphenylphosphine)dichloropalladium II are added successively under argon, then the tube is closed. The reaction mixture is heated for 4.5 h at 85° C., then concentrated under reduced pressure. The residue is purified directly on nitrile-grafted silica (eluent: A/B=(heptane/DCM 1/1)/AcEt from 0 to 100% of B), 2 g of compound is obtained in the form of a brown powder. Yield=76%. Melting point=76° C. MH+: 550 (Tr: 7.2 min, condition 1).

$^1$H NMR (400 MHz, DMSO-$d_6$), δ (ppm): 8.28 (d, 1H, 7.5 Hz); 7.56 (d, 1H, 7.5 Hz); 7.53 (s, 2H); 7.32 (d, 1H, 1.3 Hz); 7.1 (d, 1H, 1.3 Hz); 5.26 (s, 2H); 4.59 (q, 2H, 6.9 Hz); 3.18 (dd, 2H, 8.2-8.04 Hz); 1.29 (t, 3H, 6.9 Hz); 0.6 (dd, 2H, 8.2-8.04 Hz); 0 36 (t, 9H, 28 Hz); 0 (s, 9H).

1.6/2-(6-Chloro-pyridin-3-yl)-N-pyridin-2-yl-acetamide

Under inert atmosphere, 6.2 g (38.5 mmol) of N,N-carbodiimidazole is added to a suspension of 6 g (35 mmol) of 2-chloropyridylacetic acid in anhydrous THF (90 ml) at room temperature. The reaction mixture is stirred at this temperature for 2 hours, then 5.4 g (57.7 mmol) of 2-aminopyridine is added and the mixture is heated for 2 hours under reflux. 200 ml of dichloromethane is added to the reaction mixture, cooled beforehand to room temperature, the organic phase thus obtained is washed with a saturated solution of ammonium chloride, then with an aqueous solution of soda (1N), dried over $Na_2SO_4$, filtered and concentrated under reduced pressure. The residue is purified by silica gel flash chromatography (eluent: A/B=dichloromethane/ethyl acetate 0% to 70% of B). 5.6 g of compound is obtained in the form of a white powder. Yield 65%. Melting point: 130° C. MH+: 248 (Tr: 5.6 min, condition 1).

$^1$H NMR (400 MHz, DMSO-$d_6$), δ (ppm): 10.81 (s, 1H); 8.35 (d, 1H, 2.3 Hz); 8.33 (ddd, 1H, 0.9-1.9-4.9 Hz); 8.03 (d, 1H, 8.2 Hz); 7.82 (dd, 1H, 2.5-8.2 Hz); 7.77 (ddd, 1H, 1.9-7.3, 8.2 Hz); 7.49 (d, 1H, 8.2 Hz); 7.11 (ddd, 1H, 0.9-4.9-7.3 Hz); 3.81 (s, 2H).

1.7/2-(6-{7-Amino-8-ethyl-5-oxo-6-[1-(2-trimethyl-silanyl-ethoxymethyl)-1H-imidazol-2-yl]-5,8-dihydro-[1,8]naphthyridin-2-yl}-pyridin-3-yl)-N-pyridin-2-yl-acetamide A solution of 0.365 g (1.5 mmol) of the compound obtained at the end of stage 1.6 and of 1.2 g (2.2 mmol) of the compound obtained at the end of stage 1.5 in anhydrous dioxane (7 ml) is degassed with argon for 10 minutes, then 0.170 g (0.23 mmol) of palladium II dichlorodi(triphenylphosphine) and 0.05 g (0.16 mmol) of triphenylarsine are added, the tube is sealed and the reaction mixture is heated at 100° C. for 18 hours. The reaction mixture is diluted with 100 ml of dichloromethane, then the organic phase is washed with a 10% aqueous ammonia solution, dried over $Na_2SO_4$, filtered and concentrated under reduced pressure. The residue is purified by silica gel flash chromatography (eluent: A/B=dichloromethane/methanol from 0% to 10% of B). 0.32 g of compound is obtained, in the form of a yellow powder. Yield: 37%. MH+: 597 (Tr: 6.1 min, condition 1)

1.8/2-{6-[7-Amino-8-ethyl-6-(1H-imidazol-2-yl)-5-oxo-5,8-dihydro-[1,8]naphthyridin-2-yl]-pyridin-3-yl}-N-pyridin-2-yl-acetamide hydrochloride (compound 2)

Under inert atmosphere, 1 ml of trifluoroacetic acid in solution in 0.5 ml of dichloromethane is added dropwise to a suspension of 0.2 g (0.34 mmol) of the compound obtained at the end of stage 1.7 in suspension in dichloromethane (1 ml), cooled to 0° C. The reaction mixture is stirred at this temperature for 10 minutes, then at room temperature for 5 hours, then at 10° C. overnight. The mixture is then poured into a solution of $Na_2CO_3$ (2N) (6 ml), previously cooled, the yellow precipitate formed is filtered and rinsed with water, then dried under vacuum over $P_2O_5$. The solid is purified by silica gel flash chromatography (eluent: A/B=dichloromethane/(methanol/1% $NH_4OH$), from 0% to 10% of B). 0.14 g of compound is obtained in the form of a yellow powder. Yield 87%. 0.1 ml of a concentrated HCl solution (35%) is added dropwise to 0.14 g (0.3 mmol) of this compound in suspension in methanol, the mixture is then stirred at room temperature for 45 minutes, then concentrated under reduced pressure. The solid is triturated in diethyl ether, filtered and dried under vacuum over $P_2O_5$. 0.15 g of hydrochloride compound is thus obtained in the form of beige powder. Yield: 86%. Melting point=200° C. MH+ 467.2 (Tr: 5.49 min, condition 1)

$^1$H NMR (400 MHz, DMSO-$d_6$), δ (ppm): 11.47 (s, 1H); 8.76 (d, 1H, 1.9 Hz); 8.59 (d, 1H, 8 Hz); 8.52 (d, 1H, 8.2 Hz); 8.39 (d, 1H, 8 Hz); 8.36 (m, 1H); 8.08 (dd, 1H, 2-8.3 Hz); 8.03 (d, 1H, 8.3 Hz); 7.92 (m, 1H); 7.82 (s broad, 1H+1HCl); 7.66 (s, 2H); 7.22 (m, 1H); 5.52 (s, 2H+2HCl); 4.75 (m, 2H); 4.0 (s, 2H); 1.37 (t, 3H, 6.85 Hz).

Example 2

2-{4-[7-Amino-8-ethyl-6-(1H-imidazol-2-yl)-5-oxo-5,8-dihydro-[1,8]naphthyridin-2-yl]-phenyl}-N-(4-cyclopropyl-morpholin-3-ylmethyl)-acetamide (compound 3)

2.1/ethyl [4-(4,4,5,5-tetramethyl-1,3,2-dioxaborolan-2-yl)phenyl]acetate

A mixture of 9.5 g (33 mmol) of (4-iodo-phenyl)-ethyl acetate and of 9.2 g (36 mmol) of bispinacolatodiborane in solution in anhydrous dimethylsulphoxide (65 ml) is degassed with argon for 15 minutes, then 28 g (98 mmol) of potassium acetate and 1.34 g (1.6 mmol) of palladium dichloro(phosphinoferrocene) are added and the reaction mixture is heated at 55° C. for 1.5 h under argon. The reaction mixture is diluted with 220 ml of ethyl acetate, then the organic phase is washed three times with water (200 ml), then dried over $Na_2SO_4$, and concentrated under reduced pressure. 11 g of compound is obtained in the form of a brown oil, but is used as it is in the next stage. MH+: 291.2 (Tr: 9.4 min, condition 1)

2.2/(4-{7-Amino-8-ethyl-5-oxo-6-[1-(2-trimethylsilanyl-ethoxymethyl)-1H-imidazol-2-yl]-5,8-dihydro-[1,8]naphthyridin-2-yl}-phenyl)-acetic acid In a tube, a suspension of 0.7 g (2.4 mmol) of the compound obtained at the end of stage 2.1, 0.5 g (1.2 mmol) of the compound obtained at the end of stage 1.4 and 3.3 ml of a saturated solution of hydrogen carbonate in 7 ml of a mixture of DME/ethanol (2/1), is degassed with argon for 10 minutes, then 0.08 g (0.07 mmol) of palladium tetrakistriphenylphosphine is added and the tube is sealed. The reaction mixture is heated at 170° C. for 15 minutes in a microwave (Biotage initiator). The reaction mixture is then taken up in water, and acidified by adding 1N HCl solution. The solid is collected by filtration, rinsed with water and then dried over $P_2O_5$ under vacuum. 0.87 g of product is obtained in the form of a mixture of acid and ester. This mixture is used directly in the next stage.

0.1 g (2.4 mmol) of lithium hydroxide monohydrate is added to 0.87 g of the mixture of acid and ester obtained at the end of the preceding stage, in suspension in a solvent mixture THF/water/methanol (1/1/1). The reaction mixture is heated at 70° C. for 5 hours. 3.5 ml of water is added to the reaction mixture cooled to room temperature, followed by addition of HCl solution (1N) to pH 1. The solid is collected by filtration, rinsed with dichloromethane, then dried over $P_2O_5$ under vacuum. 0.4 g of product is thus isolated, without any other purification, in the form of grey powder. Yield: 62% for the two stages. Melting point: 220° C. MH$^+$: 467.2 (Tr: 5.49 min, condition 1).

$^1$H NMR (400 MHz, DMSO-d$_6$), δ (ppm): 14.42 (s, 1H); 12.46 (s, 1H); 8.46 (d, 1H, 7.2 Hz); 8.19 (d, 2H, 7.2 Hz); 8.02 (d, 1H, 7.2 Hz); 7.89 (s, 1H); 7.83 (s, 1H); 7.58 (s, 2H); 7.47 (d, 2H, 7.2 Hz); 5.35 (s, 2H); 4.68 (m, 2H); 3.7 (s, 2H); 3 42 (m, 2H); 1.37 (m, 3H); 0.77 (m, 2H); −0.11 (s, 9H).

2.3/4-Cyclopropyl-morpholine-3-carboxamide 2.9 g of molecular sieve 3A, 4.3 g (72 mmol) of acetic acid, 7.6 g (43.2 mmol) of 2(1-ethoxy-cyclopropyl)oxy]trimethylsilane and 4.4 g (31.7 mmol) of sodium cyanoborohydride are added successively to 1.2 g (7.2 mmol) of morpholine-3-carboxylic acid amide hydrochloride (WO2005026156 Hennequin L. F. A. et al.) in solution in methanol (36 ml). The reaction mixture is heated at 70° C. for 3.5 hours, then cooled to room temperature and filtered. The filtrate is concentrated under reduced pressure, then the residue is taken up in dichloromethane (200 ml) and washed 3 times with an aqueous solution of NaOH (1N) (100 ml). The organic phase is dried over $Na_2SO_4$, filtered and then concentrated under reduced pressure. 0.58 g of product is obtained, in the form of a white powder. Yield 47%. Melting point 116° C. MH$^+$: 171 (Tr: 1.03 min, condition 2).

$^1$H NMR (250 MHz, DMSO-d$_6$), δ (ppm):7.33 (s, 1H); 6.98 (s, 1H); 3.67-3.43 (m broad, 4H); 2.97 (dd, 2H, 7.3-3.6 Hz); 2.35 (ddd, 1H, 11.7-8.3-3.4 Hz); 1.89 (ddd, 1H, 10.3-6.6-3.6 Hz); 0.56-0.22 (m broad, 4H).

2.4/1-(4-cyclopropylmorpholin-3-yl)methanamine hydrochloride

Under inert atmosphere, 13.6 ml (13.6 mmol) of a solution (1N) of triborohydride complexed with tetrahydrofuran in THF is added dropwise to a solution of 0.58 g (3.4 mmol) of the compound obtained at the end of stage 2.3, in anhydrous THF, cooled to 0° C. The reaction mixture is heated at 70° C. for 3 h. 15 ml of a solution (1N) of HCl is added to the reaction mixture cooled to room temperature, after 30 min of stirring the aqueous phase is decanted and extracted twice with ether (15 ml) then basified by adding soda solution (1N). The aqueous phase is then extracted with ethyl acetate 4 times (20 ml) and with dichloromethane 4 times (20 ml). The combined organic phases are dried over $Na_2SO_4$, filtered and concentrated under reduced pressure. The residue is taken up in methanol (4 ml) and 3.4 ml of a solution of HCl (1N) in ether is added, the solution is stirred for 30 minutes then 5 ml of ether is added, the solid formed is collected by filtration and dried under vacuum over $P_2O_5$. 0.51 g of product is obtained, in the form of a white powder. Yield 78%. MH$^+$: 157 (Tr: 0.4 min, condition 2).

$^1$H NMR (400 MHz, DMSO-d$_6$), δ (ppm): 11.67 (s, 1H); 8.07 (m, 2H); 4.09 (m, 1H); 3.94 (m, 1H); 3.74 (m, 2H); 3.54 (m, 2H); 3.36 (m, 1H); 3.2 (m, 1H); 2.99 (m, 1H); 1.25 (m, 1H); 1.09-0.72 (m, 4H).

2.5/2-{4-[7-amino-8-ethyl-5-oxo-6-(1-{[2-(trimethylsilyl)ethoxy]methyl}-1H-imidazol-2-yl)-5,8-dihydro-1,8-naphthyridin-2-yl]phenyl}-N-[(4-cyclopropylmorpholin-3-yl)methyl]acetamide Under inert atmosphere, 0.4 ml (2.3 mmol) of diisopropyl ethyl amine is added to 0.4 g (0.8 mmol) of the compound obtained at the end of stage 2.2, in suspension in DMF (8 ml); after dissolution, the reaction mixture is cooled to 0° C. then a solution, in DMF (2 ml), of 0.18 g (0.94 mmol) of the compound obtained at the end of stage 2.4 and of 0.2 ml (1.2 mmol) of diisopropyl ethyl amine is added, followed by addition of 0.275 g (0.86 mmol) of BTUT. The reaction mixture is stirred at room temperature for 3 hours, then concentrated to dryness. The residue is purified directly by silica gel flash chromatography (eluent: NB=dichloromethane/methanol (1% NH4OH) gradient from 0 to 10% of B). 0.34 g of product is obtained in the form of a yellow powder. Yield: 65%. Melting point: 116° C.

MH+: 657 (Tr: 5.51 min, condition 1)

2.6/2-{4-[7-Amino-8-ethyl-6-(1H-imidazol-2-yl)-5-oxo-5,8-dihydro-[1,8]naphthyridin-2-yl]-phenyl}-N-(4-cyclopropyl-morpholin-3-ylmethyl)-acetamide hydrochloride (compound 3)

1.4 ml (19 mmol) of trifluoroacetic acid in solution in 0.4 ml of dichloromethane is added dropwise to 0.3 g (0.47 mmol) of the compound obtained at the end of stage 2.5, in solution in 0.4 ml dichloromethane, cooled to −10° C., then the reaction mixture is stirred at 5° C. overnight and then poured into a solution of $Na_2CO_3$ (2M) (10 ml) in the cold (ice bath). The yellow precipitate formed is collected by filtration and rinsed with water, and then dried over $P_2O_5$ under vacuum. The 0.18 g of solid is taken up in 2 ml of methanol and 70 μl of a 36% solution of HCl is added, the mixture is stirred for one hour at room temperature, then concentrated under vacuum. The residue is purified by flash chromatography on a C8 reverse phase column (eluent: water HCl (N/1000). 0.034 g of product is obtained in the form of a yellow powder. Yield=16%. Melting point: 210° C. MH+: 528.2 (Tr: 4.78 min, condition 1).

$^1$H NMR (400 MHz, DMSO-d$_6$), δ (ppm): 11.29 (s, 1H); 8.52 (d, 1H, 8.2 Hz); 8.48 (s, 1H exchangeable); 8.18 (d, 2H+1H exchangeable, 8.3 Hz); 7.99 (d, 1H+1H exchangeable, 8.2 Hz); 7.54 (s, 2H); 7.48 (d, 2H, 8.3 Hz); 4.7 (q broad, 2H, 7 Hz); 3.91 (m, 3H); 3.73 (m, 1H); 3.58 (s, 3H); 3.47 (m, 2H); 3.34 (m, 2H); 2.93 (m, 1H); 1.36 (t, 3H, 7 Hz); 1.25 (m, 1H); 0.95 (m, 2H); 0.81 (m, 1H).

Example 3

2-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-propionamide (compound 47)

3.1/ethyl 2-[4-(4,4,5,5-tetramethyl-1,3,2-dioxaborolan-2-yl)phenyl]propanoate

Same procedure as that described in example 2, stage 2.1, starting from 0.6 g (2 mmol) of ethyl 2-(4-iodophenyl)propanoate in solution in anhydrous DMSO (4 ml), 0.57 g (2.2 mmol) of bispinacolatodiborane, 1.7 g (6 mmol) of potassium acetate and 83 mg (0.1 mmol) of palladium dichloro(phosphinoferrocene). 0.9 g of compound is obtained in the form of a brown oil, used as it is in the next stage. MH$^+$: 305 (Tr: 9.9 min, condition 1)

3.2/2-{4-[7-amino-8-ethyl-5-oxo-6-(1-{[2-(trimethylsilyl)ethoxy]methyl}-1H-imidazol-2-yl)-5,8-dihydro-1,8-naphthyridin-2-yl]phenyl}propanoic acid Same procedure as that described in example 2, stage 2.2, starting from 0.57 g (1.4 mmol) of the compound obtained at the end of stage 3.1, 0.82 g (2.7 mmol) of the compound obtained at the end of stage 1.4, 94 mg (0.08 mmol) of palladium tetrakistriphenylphosphine, 4 ml of a saturated solution of hydrogen carbonate in a mixture of DME/ethanol (2/1) (7 ml), 1.1 g of product is obtained in the form of a mixture of acid and ester. This mixture is used directly in the next stage, in the presence of 0.16 g (3.8 mmol) of lithium hydroxide monohydrate suspension in a solvent mixture THF/water/methanol (1/1/1) (10 ml). 0.4 g of product is obtained in the form of brown powder. Yield: 39% for the two stages. Melting point: 248° C. MH+ 534.1 (Tr: 6.5 min, condition 1)

3.3/2-{4-[7-amino-8-ethyl-5-oxo-6-(1-{[2-(trimethylsilyl)ethoxy]methyl}-1H-imidazol-2-yl)-5,8-dihydro-1,8-naphthyridin-2-yl]phenyl}-N-(pyridin-4-ylmethyl)propanamide Same procedure as that described in example 2, stage 2.5, starting from 0.3 g (0.56 mmol) of the compound obtained at the end of stage 3.2, 0.25 g (2.25 mmol) of 1-(pyridin-4-yl)methanamine, 0.36 g (1.1 mmol) of BTUT and 0.14 g (1.1 mmol) of diisopropylethylamine in anhydrous DMF (5 ml), 0.29 g of product is obtained in the form of yellow powder. Yield: 82%. Melting point: 140° C. MH+: 624 (Tr: 5.66 min, condition 1).

3.4/2-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-propionamide (compound 47)

Same procedure as that described in example 2, stage 2.6, starting from 0.26 g (0.42 mmol) of the compound obtained at the end of stage 3.3 in solution in 1.2 ml of dichloromethane, 1.3 ml (17 mmol) of trifluoroacetic acid in solution in 0.5 ml of dichloromethane. 0.051 g of product is obtained in the form of a yellow powder. Yield=24%. Melting point: 186° C. MH+: 494.2 (Tr: 5.05 min, condition 1).

$^1$H NMR (400 MHz, DMSO-$d_6$), δ (ppm): 13.20 (s, 1H); 11.51 (s, 1H); 8.62 (m, 2H); 8.45 (dd, 2H, 4.5, 1.5 Hz); 8.29 (d, 2H, 8.2 Hz); 8.02 (s broad, 1H exchangeable); 7.97 (d, 1H, 8.2 Hz); 7.53 (d, 2H, 8.2 Hz); 7.16 (m, 3H); 7.04 (m, 1H); 4.72 (m, 2H); 4.29 (d, 2H, 6 Hz); 3.81 (q, 1H, 7 Hz); 1.45 (d, 3H, 7.1 Hz); 1.38 (t, 3H, 7 Hz).

Example 4

4-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-butyramide (compound 49)

4.1/4-[4-(4,4,5,5-tetramethyl-1,3,2-dioxaborolan-2-yl)phenyl]butanoic acid

Same procedure as that described in example 2, stage 2.1, starting from 0.3 g (1 mmol) of 4-(4-iodophenyl)butanoic acid in solution in anhydrous DMSO (2 ml), 0.29 g (1.1 mmol) of bispinacolatodiborane, 0.3 g (3.1 mmol) of potassium acetate and 42 mg (0.05 mmol) of palladium dichloro (phosphinoferrocene). 0.21 g of compound is obtained in the form of a brown oil, used as it is in the next stage. MH+: 291 (Tr: 8.35 min, condition 1)

4.2/4-[4-(7-amino-8-ethyl-5-oxo-6-{1-[2-(trimethylsilyl)ethoxy]-1H-imidazol-2-yl}-5,8-dihydro-1,8-naphthyridin-2-yl)phenyl]butanoic acid Same procedure as that described in example 2, stage 2.2, from 0.17 g (0.57 mmol) of the compound obtained at the end of stage 4.1, 0.18 g (0.44 mmol) of the compound obtained at the end of stage 1.4, 25 mg (0.02 mmol) of palladium tetrakistriphenylphosphine, 1.2 ml of a saturated solution of hydrogen carbonate in a mixture of DME/ethanol (2/1) (3 ml), 0.25 g of product is obtained in the form of a brown oil used as it is in the next stage. MH+: 548 (Tr: 6.5 min, condition 1)

4.3/4-[4-(7-amino-8-ethyl-5-oxo-6-{1-[2-(trimethylsilyl)ethoxy]-1H-imidazol-2-yl}-5,8-dihydro-1,8-naphthyridin-2-yl)phenyl]-N-(pyridin-4-ylmethyl)butanamide Same procedure as that described in example 2, stage 2.5, starting from 0.5 g (0.46 mmol) of the compound obtained at the end of stage 4.2, 0.2 g (1.8 mmol) of 1-(pyridin-4-yl)methanamine, 0.3 g (0.9 mmol) of BTUT and 0.12 g (0.9 mmol) of diisopropylethylamine in anhydrous DMF (5 ml), 0.1 g of product is obtained in the form of beige powder. Yield: 34%. Melting point: 223° C. MH+: 638 (Tr: 5.75 min, condition 1).

4.4/4-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-butyramide (compound 49)

Same procedure as that described in example 2, stage 2.6, starting from 0.095 g (0.15 mmol) of the compound obtained at the end of stage 4.3 in solution in 0.5 ml of dichloromethane, 0.44 ml (6 mmol) of trifluoroacetic acid in solution in 0.3 ml of dichloromethane. 0.045 g of product is obtained in the form of a yellow powder. Yield=60%. Melting point: 240° C. MH+: 508.2 (Tr: 4.97 min, condition 1).

$^1$H NMR (400 MHz, DMSO-$d_6$), δ (ppm): 13.21 (s, 1H); 11.48 (s, 1H); 8.61 (d, 1H, 8 Hz); 8.49 (d, 2H, 4.5 Hz); 8.44 (t, 1H, 6 Hz); 8.45 (s broad, 1H exchangeable); 8.17 (d, 2H, 8.1 Hz); 7.97 (d, 1H, 8.1 Hz); 7.39 (t, 2H, 8.1 Hz); 7.24 (d, 1H, 4.8 Hz); 7.15 (s, 1H); 7.03 (s, 1H); 4.72 (m, 2H); 4.30 (d, 2H, 5.8 Hz); 3.81 (q, 1H, 7 Hz); 2.68 (t, 2H, 7.5 Hz); 2.24 (t, 2H, 7.3 Hz); 1.92 (m, 2H); 1.38 (t, 3H, 7 Hz).

Example 5

2-{4-[7-Amino-8-ethyl-6-(4-methyl-1H-imidazol-2-yl)-5-oxo-5,8-dihydro-[1,8]naphthyridin-2-yl]-phenyl}-N-pyridin-4-ylmethyl-acetamide (compound 50)

5.1/[1-(2-Trimethylsilanyl-ethoxymethyl)-1H-(4-methyl-1H-imidazol-2-yl)acetonitrile Same procedure as that described in example 1, stage 1.3, starting from 4.6 g (19 mmol) of [1-(2-Trimethylsilanyl-ethoxymethyl)-1H-(4-methyl-1H-imidazol-2-yl)carbaldehyde, 4 g (20.3 mmol) of TOSMIC and 4.3 g of potassium tert-butylate in solution in anhydrous DME (32 ml). 2.2 g of compound is obtained in the form of a yellow oil as 70/30 mixture of τ and π regioisomers (Yield 45%. MH+: 252 (Tr: 6.38 and 6.55 min, condition 1)

5.2/2-amino-7-chloro-1-ethyl-3-(4-methyl-1-{[2-(trimethylsilyl)ethoxy]methyl}-1H-imidazol-2-yl)-1, 8-naphthyridin-4(1H)-one Same procedure as that described in example 1, stage 1.4, starting from 1 g (4 mmol) of the compound obtained at the end of stage 5.1, 0.8 g (4 mmol) of the compound obtained at the end of stage 1.2 and 1.15 g (10 mmol) of potassium tert-butylate in solution in anhydrous THF (13 ml). 0.42 g of product is obtained in the form of a beige powder. Yield 24%. Melting point: 120° C. MH+: 435 (Tr: 10.5 and 10.6 min, condition 1)

5.3/{4-[7-amino-8-ethyl-6-(4-methyl-1-{[2-(trimethylsilyl)ethoxy]methyl}-1H-imidazol-2-yl)-5-oxo-5, 8-dihydro-1,8-naphthyridin-2-yl]phenyl}acetic acid Same procedure as that described in example 2, stage 2.2, starting from 0.42 g (1 mmol) of the compound obtained at the end of stage 5.2, 0.84 g (2.9 mmol) of the compound obtained at the end of stage 2.1, 67 mg (0.06 mmol) of palladium tetrakistriphenylphosphine, 1.2 ml of a saturated solution of hydrogen carbonate in a solvent mixture DME/EtOH (2/1) (7 ml). 0.69 g of product is obtained in the form of a mixture of acid and ester. This mixture is used directly in the next stage, in the presence of 0.12 g (3 mmol) of lithium hydroxide monohydrate suspension in a solvent mixture THF/water/methanol (1/1/1) (7 ml). 0.67 g of product is obtained in the form of brown powder used without purification. MH+: 534 (Tr: 4.38 min, condition 1).

5.4/2-{4-[7-amino-8-ethyl-6-(4-methyl-1-{[2-(trimethylsilyl)ethoxy]methyl}-1H-imidazol-2-yl)-5-oxo-5,8-dihydro-1,8-naphthyridin-2-yl]phenyl}-N-(pyridin-4-ylmethyl)acetamide Same procedure as that described in example 2, stage 2.5, starting from 0.67 g (1.2 mmol) of the compound obtained at the end of stage 5.3, 0.55 g (5 mmol) of 1-(pyridin-4-yl)methanamine, 0.8 g (2.5 mmol) of BTUT and 0.32 g (2.4 mmol) of diisopropylethylamine in anhydrous DMF (12 ml), 0.22 g of product is obtained in the form of yellow powder. Yield: 28%. MH+: 624 (Tr: 5.6 min, condition 1).

5.5/2-{4-[7-Amino-8-ethyl-6-(4-methyl-1H-imidazol-2-yl)-5-oxo-5,8-dihydro-[1,8]naphthyridin-2-yl]-phenyl}-N-pyridin-4-ylmethyl-acetamide salt of TFA (compound Same procedure as that described in example 2, stage 2.6, starting from 0.22 g (0.36 mmol) of the compound obtained at the end of stage 5.4 in solution in 0.5 ml of dichloromethane, 1.6 ml (14 mmol) of trifluoroacetic acid in solution in 0.5 ml of dichloromethane, purification by HPLC. 0.124 g of product, in the form of salt of trifluoroacetic acid, is obtained in the form of a yellow powder. Yield=60%. Melting point: 144° C. MH+: 494 (Tr: 4.54 min, condition 1).
$^1$H NMR (400 MHz, DMSO-d$_6$), δ (ppm): 8.83 (t, 1H, 5.9 Hz); 8.68 (d, 2H, 5.2 Hz); 8.52 (d, 1H, 8.1 Hz); 8.19 (d, 2H, 8.3 Hz); 8.09 (s broad, 1H exchangeable); 8.0 (d, 1H, 8.2 Hz); 7.6 (d, 2H, 5.9 Hz); 7.5 (d, 2H, 8.3 Hz); 7.2 (s, 1H); 4.7 (m, 2H); 5.4-4 (s broad, 2H exchangeable); 4.46 (d, 2H, 6 Hz); 3.66 (s, 2H); 2.3 (s, 3H); 1.4 (t, 3H, 7 Hz)

Example 6

2-{4-[7-Amino-8-cyclopropylmethyl-6-(1H-imidazol-2-yl)-5-oxo-5,8-dihydro-[1,8]naphthyridin-2-yl]-phenyl}-N-pyridin-4-ylmethyl-acetamide (compound 51)

6.1/6-chloro-2-[(cyclopropylmethyl)amino]pyridine-3-carboxylic acid

In a sealable tube, 3 g (42 mmol) of cyclopropylmethylamine is added to 3 g (14 mmol) of 2,6-dichloronitinic acid in solution in tert-butanol (14 ml), the tube is sealed and heated at 170° C. for 30 minutes in a Biotage Initiator microwave. The reaction mixture is cooled to room temperature, diluted in dichloromethane (100 ml) and washed with a 10% aqueous solution of acetic acid (12 ml). The organic phase is dried over Na$_2$SO$_4$, filtered, concentrated and dried under vacuum. 3.4 g of product is obtained in the form of an orange oil. Yield is quantitative. MH+: 227 (Tr: 4.54 min, condition 1)

6.2/6-chloro-2-[(cyclopropylmethyl)amino]pyridine-3-carbonyl fluoride

Same procedure as that described in example 1, stage 1.2, starting from 0.43 g (2 mmol) of the compound obtained at the end of stage 6.1 in solution in 4 ml of dichloromethane, 0.52 g (3.8 mmol) of cyanuric fluoride, and 0.4 g (3.8 mmol) of triethylamine. The product, obtained in the form of a green oil, is used without purification in the next stage.

6.3/2-amino-7-chloro-1-(cyclopropyl methyl)-3-(1-{[2-(trimethylsilyl)ethoxy]methyl}-1H-imidazol-2-yl)-1,8-naphthyridin-4(1H)-one Same procedure as that described in example 1, stage 1.4, starting from 0.43 g (2 mmol) of the compound obtained at the end of stage 6.2, 0.5 g (2 mmol) of the compound obtained at the end of stage 1.3 in solution in 6 ml of anhydrous THF and 0.55 g (5 mmol) of potassium tert-butylate and 0.4 g (3.8 mmol) of triethylamine. 0.5 g of product is obtained in the form of a brown powder. Yield=60%. Melting point: 70° C. MH+: 447 (Tr: 6.68 min, condition 1).

6.4/{4-[7-amino-8-(cyclopropylmethyl)-5-oxo-6-(1-{[2-(trimethylsilyl)ethoxy]methyl}-1H-imidazol-2-yl)-5,8-dihydro-1,8-naphthyridin-2-yl]phenyl}acetic acid Same procedure as that described in example 2, stage 2.2, starting from 0.44 g (1 mmol) of the compound obtained at the end of stage 6.3, 1 g (3.5 mmol) of the compound obtained at the end of stage 2.1, 70 mg (0.06 mmol) of palladium tetrakistriphenylphosphine, 2.8 ml of a saturated solution of hydrogen carbonate in a solvent mixture DME/EtOH (2/1) (8 ml). 0.8 g of product is obtained in the form of a mixture of acid and ester. This mixture is used directly in the next stage, in the presence of 0.15 g (3.6 mmol) of lithium hydroxide monohydrate in suspension in a solvent mixture THF/water/methanol (1/1/1) (9 ml). 0.91 g of product is obtained in the form of brown powder, used without purification in the next stage. MH+: 546 (Tr: 4.39 min, condition 1).

6.5/2-{4-[7-amino-8-(cyclopropylmethyl)-5-oxo-6-(1-{[2-(trimethylsilyl)ethoxy]methyl}-1H-imidazol-2-yl)-5,8-dihydro-1,8-naphthyridin-2-yl]phenyl}-N-(pyridin-4-ylmethyl)acetamide Same procedure as that described in example 2, stage 2.5, starting from 0.9 g (1.7 mmol) of the compound obtained at the end of stage 6.4, 0.73 g (6.7 mmol) of 1-(pyridin-4-yl) methanamine, 1.1 g (3.3 mmol) of BTUT and 0.43 g (3.3 mmol) of diisopropylethylamine in anhydrous DMF (17 ml), 0.3 g of product is obtained in the form of beige powder. Yield: 28%. Melting point: 114° C. MH$^+$: 635 (Tr: 5.6 min, condition 1).

6.6/2-{4-[7-Amino-8-cyclopropylmethyl-6-(1H-imidazol-2-yl)-5-oxo-5,8-dihydro-[1,8]naphthyridin-2-yl]-phenyl}-N-pyridin-4-ylmethyl-acetamide salt of TFA (compound 51)

Same procedure as that described in example 2, stage 2.6, starting from 0.28 g (0.45 mmol) of the compound obtained at the end of stage 6.5 in solution in 1.5 ml of dichloromethane, 1.3 ml (18 mmol) of trifluoroacetic acid in solution in 0.8 ml of dichloromethane. 0.2 g of product is obtained in the form of a yellow powder. Yield=60%. Melting point: 118° C. MH$^+$: 506 (Tr: 4.96 min, condition 1).
$^1$H NMR (400 MHz, DMSO-d$_6$), δ (ppm): 8.85 (t, 1H, 5.7 Hz); 8.7 (d, 2H, 5.8 Hz); 8.58 (s broad, 1H exchangeable); 8.56 (d, 1H, 8.1 Hz); 8.16 (d, 2H, 8.1 Hz); 8.0 (d, 1H, 8.2 Hz); 7.64 (d, 2H, 5.8 Hz); 7.50 (d, 2H, 8.2 Hz); 7.4 (s, 2H); 4.7 (m, 2H); 5.4-4.0 (s broad, 2H exchangeable); 4.50 (d, 2H, 5.8 Hz); 3.67 (s, 2H); 1.4 (m, 1H); 0.6 (m, 2H); 0.5 (m, 2H).

Example 7

2-{5-[7-Amino-8-ethyl-6-(1H-imidazol-2-yl)-5-oxo-5,8-dihydro-[1,8]naphthyridin-2-yl]-pyridin-2-yl}-N-pyridin-4-ylmethyl-acetamide (compound 53)

7.1/2-(5-bromopyridin-2-yl)-N-(pyridin-4-ylmethyl)acetamide

Same procedure as that described in example 2, stage 2.5, starting from 0.33 g (1.5 mmol) of (5-bromo-pyridin-2-yl)-acetic acid (a synthesis of which is described in Tetrahedron, 1997, 53(24) 8257-8268 Gurnos J. et al.), 0.67 g (6.1 mmol) of 1-(pyridin-4-yl)methanamine, 1 g (3 mmol) of BTUT and 0.4 g (3 mmol) of diisopropylethylamine in anhydrous DMF (15 ml), 0.59 g of product is obtained in the form of beige powder, used without purification in the next stage. MH$^+$: 307 (Tr: 2.92 min, condition 1).

7.2/2-{5-[7-amino-8-ethyl-5-oxo-6-(1-{[2-(trimethylsilyl)ethoxy]methyl}-1H-imidazol-2-yl)-5,8-dihydro-1,8-naphthyridin-2-yl]pyridin-2-yl}-N-(pyridin-4-ylmethyl)acetamide Same procedure as that described in example 1, stage 1.7, starting from 0.58 g (1.9 mmol) of the compound obtained at the end of stage 7.1, 1.2 g (2.3 mmol) of the compound obtained at the end of stage 1.5, 220 mg (0.3 mmol) of palladium II dichlorodi(triphenylphosphine) and 65 mg (0.21 mmol) of triphenylarsine in solution in 9 ml of anhydrous dioxane. 0.38 g of compound is obtained, in the form of a yellow powder. Yield: 32%. MH$^+$: 611 (Tr: 5.43 min, condition 1).

7.3/2-{5-[7-Amino-8-ethyl-6-(1H-imidazol-2-yl)-5-oxo-5,8-dihydro-[1,8]naphthyridin-2-yl]-pyridin-2-yl}-N-pyridin-4-ylmethyl-acetamide (compound 53)

Same procedure as that described in example 1, stage 1.8, starting from 0.36 g (0.6 mmol) of the compound obtained at the end of stage 7.2 in solution in 1.8 ml of dichloromethane, 1.8 ml (24 mmol) of trifluoroacetic acid in solution in 1 ml of dichloromethane. 0.314 g of product is obtained in the form of a yellow powder. Yield=78%. Melting point: 120° C. MH$^+$: 481 (Tr: 4.32 min, condition 1).
$^1$H NMR (400 MHz, DMSO-d$_6$), δ (ppm): 9.38 (d, 1H, 2.3 Hz); 8.93 (t, 1H, 6 Hz); 8.77 (d, 2H, 6.3 Hz); 8.68 (s broad, 1H exchangeable); 8.62 (d, 1H, 8 Hz); 8.57 (dd, 1H, 8.2, 2.4 Hz); 8.1 (d, 1H, 8 Hz); 7.77 (d, 2H, 6 Hz); 7.60 (d, 1H, 8.2 Hz); 7.41 (s, 2H); 4.71 (m, 2H); 5.4-4 (s broad, 2H exchangeable); 4.54 (d, 2H, 6 Hz); 3.90 (s, 2H); 1.38 (t, 3H, 7 Hz).

Example 8

2-{4-[7-Amino-8-ethyl-6-(1H-imidazol-2-yl)-5-oxo-5,8-dihydro-[1,8]naphthyridin-2-yl]-2-fluoro-phenyl}-N-(1-ethyl-pyrrolidin-2-ylmethyl)-acetamide (compound 56)

8.1/(4-bromo-2-fluorophenyl)acetic acid 0.09 g of lithium hydroxide monohydrate is added to 0.37 g (1.4 mmol) of ethyl ester of (4-bromo-2-fluorophenyl)acetic acid in solution in 8 ml of a solvent mixture THF/methanol/water (1/1/1), and the reaction mixture is stirred for 3 h at room temperature. The reaction mixture is acidified with 1N HCl solution, then extracted with dichloromethane (20 ml). The organic phases are combined, dried over Na$_2$SO$_4$, filtered and concentrated under reduced pressure. 0.3 g of product is obtained in the form of gum and is used without purification in the next stage. Yield 91%.

8.2/(4-bromo-2-fluorophenyl)acetyl chloride 0.3 g (2.4 mmol) of oxalyl chloride is added to 0.28 g (1.2 mmol) of the compound obtained at the end of stage 8.1 in solution in 7 ml of 1,2-dichloroethane. The reaction mixture is stirred at room temperature for 1.5 h and then concentrated under reduced pressure. 0.322 g of compound is obtained in the form of an oil and is used without purification in the next stage.

8.3/2-(4-bromo-2-fluorophenyl)-N-[(1-ethylpyrrolidin-2-yl)methyl]acetamide 0.15 g (1.2 mmol) of 1-(1-ethylpyrrolidin-2-yl)methanamine is added to 0.3 g (1.2 mmol) of the compound obtained at the end of stage 8.2 in solution in 8 ml of dichloromethane cooled by an ice bath and under inert atmosphere, and it is stirred for a further 4 h. The reaction mixture is diluted with 20 ml of dichloromethane and washed with 20 ml of water, then the organic phase is dried over Na$_2$SO$_4$, filtered and concentrated under reduced pressure. The residue is then purified by silica gel flash chromatography (eluent: A/B=dichloromethane/methanol (1% NH4OH) gradient from 0 to 10% of B). 0.2 g of product is obtained in the form of a beige powder. Yield: 50%. MH$^+$343 (Tr: 4.94 min, condition 1).

8.4/2-{4-[7-amino-8-ethyl-5-oxo-6-(1-{[2-(trimethylsilyl)ethoxy]methyl}-1H-imidazol-2-yl)-5,8-dihydro-1,8-naphthyridin-2-yl]-2-fluorophenyl}-N-[(1-ethylpyrrolidin-2-yl)methyl]acetamide Same procedure as that described in example 1, stage 1.7, starting from 0.074 g (0.22 mmol) of the compound obtained at the end of stage 8.3, 0.15 g (0.3 mmol) of the compound obtained at the end of stage 1.5, 24 mg (0.03 mmol) of palladium II dichlorodi(triphenylphosphine) and 8 mg (0.02 mmol) of triphenylarsine in solution in 1 ml of anhydrous dioxane. 0.063 g of compound is obtained, in the form of a yellow powder. Yield: 45%. MH⁺: 648 (Tr: 5.31 min, condition 1).

8.5/2-{4-[7-Amino-8-ethyl-6-(1H-imidazol-2-yl)-5-oxo-5,8-dihydro-[1,8]naphthyridin-2-yl]-2-fluoro-phenyl}-N-(1-ethyl-pyrrolidin-2-ylmethyl)-acetamide (compound 56)

Same procedure as that described in example 2, stage 2.6, starting from 0.055 g (0.08 mmol) of the compound obtained at the end of stage 8.4 in solution in 0.25 ml of dichloromethane, 0.25 ml (3.4 mmol) of trifluoroacetic acid in solution in 0.1 ml of dichloromethane. 0.017 g of product is obtained in the form of a yellow powder. Yield=39%. Melting point: 100° C. MH⁺: 518.3 (Tr: 4.71 min, condition 1).

$^1$H NMR (400 MHz, DMSO-$d_6$), δ (ppm): 9.15 (s, 1H); 8.62 (d, 1H, 8.1 Hz); 8.50 (t, 1H, 5.7. Hz); 8.07-8.0 (m, 3H); 7.54 (t, 1H, 8 Hz); 7.24 (s, 2H); 4.70 (m, 2H); 3.92-3.32 (m, 6H+3H exchangeable); 3.08 (m, 2H); 2.13 (m, 1H); 1.97 (m, 1H); 1.86 (m, 1H); 1.74 (m, 1H); 1.38 (t, 3H, 7 Hz); 1.22 (t, 3H, 7.2 Hz).

Compounds 1, 4, 5, 6, 7, 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 48 and 55 were synthesized following the synthesis route described in example 2; compound 9 following the synthesis route described in example 1, and compounds 52 and 54 were synthesized following the synthesis route described in example 6.

The following table presents chemical structures and physical properties of some examples of the compounds according to the invention.

In this table:
in the "salt" column:
"-" represents a compound in the form of free base, whereas
"HCl" or "TFA" signify, respectively, a compound in the form of hydrochloride or of salt of trifluoroacetic acid.
Me, Et, represent methyl and ethyl groups respectively.

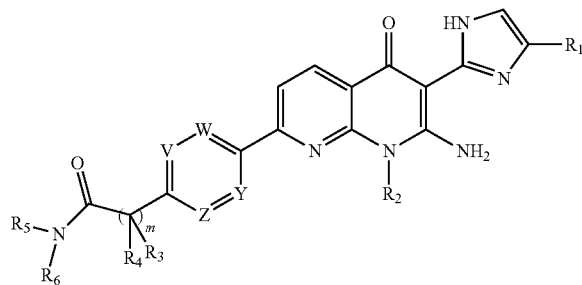

where R6 represents —(CH₂)ₙ—L

| No. | m | n | R1 | R3 | R4 | R5 | L | R2 | v | w | Y | Z | Salt | LCMS MH* |
|---|---|---|---|---|---|---|---|---|---|---|---|---|---|---|
| 1 | 1 | 0 | H | H | H | H | 2-pyridyl | Et | CH | CH | CH | CH | HCl | 466 |
| 2 | 1 | 0 | H | H | H | H | 2-pyridyl | Et | CH | CH | N | CH | HCl | 467.1 |
| 3 | 1 | 1 | H | H | H | H | N-cyclopropyl-morpholinyl | Et | CH | CH | CH | CH | HCl | 528.2 |
| 4 | 1 | 1 | H | H | H | H | N-isopropyl-morpholinyl | Et | CH | CH | CH | CH | HCl | 530 |

-continued

| # | | | | | | Structure | | | | | | | Mass |
|---|---|---|---|---|---|---|---|---|---|---|---|---|---|
| 5 | 1 | 0 | H | H | H | cyclohexyl-CH2-pyrrolidine | Et | CH | CH | CH | CH | TFA | 526.31 |
| 6 | 1 | 2 | H | H | H | H, 4-pyridyl | Et | CH | CH | CH | CH | TFA | 494.24 |
| 7 | 1 | 2 | H | H | H | Me, 4-pyridyl | Et | CH | CH | CH | CH | TFA | 508.25 |
| 8 | 1 | 0 | H | H | H | 5-methylthiazol-2-yl | Et | CH | CH | CH | CH | TFA | 486.18 |
| 9 | 1 | 2 | H | Me | H | H, 1-ethylpyrrolidin-2-yl | Et | CH | CCH3 | CH | CH | — | 514.26 |
| 10 | 1 | 0 | H | H | H | 6-methylpyridin-3-yl | Et | CH | CH | CH | CH | TFA | 480.23 |
| 11 | 1 | 1 | H | H | H | H, 1,3-dimethylpyrazol-4-yl | Et | CH | CH | CH | CH | TFA | 497.24 |
| 12 | 1 | 1 | H | H | H | H, thiazol-2-yl | Et | CH | CH | CH | CH | TFA | 486.25 |
| 13 | 1 | 1 | H | H | H | H, 5-oxopyrrolidin-2-yl | Et | CH | CH | CH | CH | TFA | 486.24 |
| 14 | 1 | 0 | H | H | H | 5-methyl-1,3,4-thiadiazol-2-yl | Et | CH | CH | CH | CH | TFA | 487.19 |
| 15 | 1 | 0 | H | H | H | 1,3,4-thiadiazol-2-yl | Et | CH | CH | CH | CH | TFA | 473.19 |
| 16 | 1 | 0 | H | H | H | 3-methylisoxazol-5-yl | Et | CH | CH | CH | CH | TFA | 470.22 |
| 17 | 1 | 2 | H | H | H | H, 1-methylpyrrolidin-2-yl | Et | CH | CH | CH | CH | TFA | 500.3 |

-continued

| | | | | | | | | | | | | | | |
|---|---|---|---|---|---|---|---|---|---|---|---|---|---|---|
| 18 | 1 | 0 | H | H | H | H | 4-methylthiazol-2-yl | Et | CH | CH | CH | CH | TFA | 486.25 |
| 19 | 1 | 1 | H | H | H | H | pyridin-4-yl | Et | CH | CH | CH | CH | TFA | 480.21 |
| 20 | 1 | 0 | H | H | H | H | 5-cyclopropyl-1,3,4-thiadiazol-2-yl | Et | CH | CH | CH | CH | TFA | 513.2 |
| 21 | 1 | 2 | H | H | H | H | pyridin-3-yl | Et | CH | CH | CH | CH | TFA | 494.28 |
| 22 | 1 | 1 | H | H | H | H | 1,3-dimethyl-1H-pyrazol-5-yl | Et | CH | CH | CH | CH | TFA | 497.25 |
| 23 | 1 | 1 | H | H | H | H | 1-methyl-1H-imidazol-4-yl | Et | CH | CH | CH | CH | TFA | 483.25 |
| 24 | 1 | 0 | H | H | H | H | pyrazin-2-yl | Et | CH | CH | CH | CH | TFA | 467.22 |
| 25 | 1 | 2 | H | H | H | H | pyridin-2-yl | Et | CH | CH | CH | CH | TFA | 494.26 |
| 26 | 1 | 0 | H | H | H | H | 5-chlorothiazol-2-yl | Et | CH | CH | CH | CH | TFA | 506.13 |
| 27 | 1 | 0 | H | H | H | H | 3,4-dimethylisoxazol-5-yl | Et | CH | CH | CH | CH | TFA | 484.27 |
| 28 | 1 | 0 | H | H | H | H | 2-methylpyridin-4-yl | Et | CH | CH | CH | CH | TFA | 480.24 |

| | | | | | | | | | | | | | |
|---|---|---|---|---|---|---|---|---|---|---|---|---|---|
| 29 | 1 | 1 | H | H | H | H | 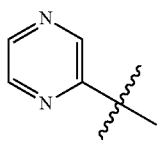 | Et | CH | CH | CH | CH | TFA | 481.25 |
| 30 | 1 | 0 | H | H | H | H | 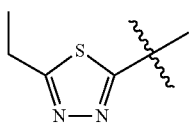 [SMILES: *c1nnc(CC)s1] | Et | CH | CH | CH | CH | TFA | 501.21 |
| 31 | 1 | 1 | H | H | H | H | 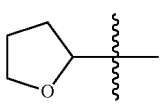 | Et | CH | CH | CH | CH | TFA | 473.27 |
| 32 | 1 | 0 | H | H | H | H | 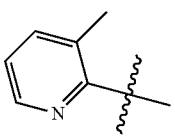 [SMILES: *c1ncccc1C] | Et | CH | CH | CH | CH | TFA | 480.24 |
| 33 | 1 | 0 | H | H | H | H | 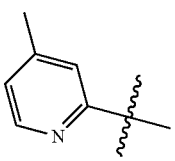 [SMILES: *c1cc(C)ccn1] | Et | CH | CH | CH | CH | TFA | 480.23 |
| 34 | 1 | 0 | H | H | H | H | 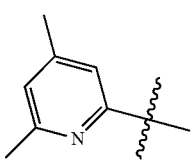 [SMILES: *c1cc(C)cc(C)n1] | Et | CH | CH | CH | CH | TFA | 494.25 |
| 35 | 1 | 0 | H | H | H | H | 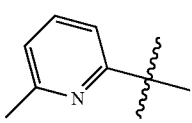 [SMILES: *c1cccc(C)n1] | Et | CH | CH | CH | CH | TFA | 480.26 |
| 36 | 1 | 1 | H | H | H | H | 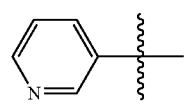 | Et | CH | CH | CH | CH | TFA | 480.24 |
| 37 | 1 | 0 | H | H | H | H | 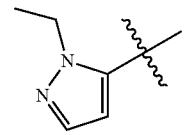 [SMILES: *c1ccnn1CC] | Et | CH | CH | CH | CH | TFA | 483.23 |
| 38 | 1 | 0 | H | H | H | H | 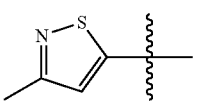 | Et | CH | CH | CH | CH | TFA | 486.2 |
| 39 | 1 | 0 | H | H | H | H | 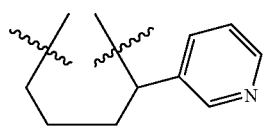 [SMILES: *CCCC(*)c1cccnc1] | Et | CH | CH | CH | CH | TFA | 520.28 |

-continued
| | | | | | | | | | | | | | | |
|---|---|---|---|---|---|---|---|---|---|---|---|---|---|---|
| 40 | 1 | 0 | H | H | H | H | 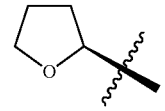 | Et | CH | CH | CH | CH | TFA | 548.29 |
| 41 | 1 | 1 | H | H | H | H | 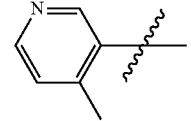 [SMILES: *c1cnccc1C] | Et | CH | CH | CH | CH | TFA | 473.22 |
| 42 | 1 | 0 | H | H | H | H | 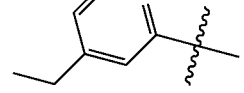 | Et | CH | CH | CH | CH | TFA | 480.23 |
| 43 | 1 | 0 | H | H | H | H | 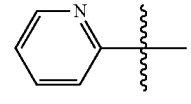 | Et | CH | CH | CH | CH | TFA | 494.26 |
| 44 | 1 | 1 | H | H | H | Me | 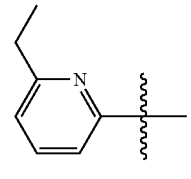 [SMILES: *c1cccc(CC)n1] | Et | CH | CH | CH | CH | TFA | 508.26 |
| 45 | 1 | 0 | H | H | H | H | 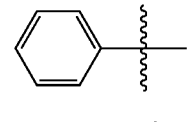 | Et | CH | CH | CH | CH | TFA | 494.25 |
| 46 | 1 | 1 | H | H | H | H | 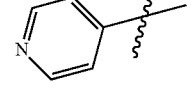 | Et | CH | CH | CH | CH | TFA | 479.15 |
| 47 | 1 | 1 | H | Me | H | H | 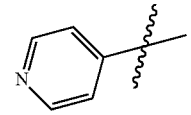 [SMILES: *c1ccncc1] | Et | CH | CH | CH | CH | — | 494.23 |
| 48 | 0 | 1 | H | H | H | H | 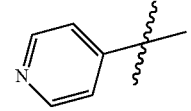 [SMILES: *c1ccncc1] | Et | CH | CH | CH | CH | — | 466.0 |
| 49 | 3 | 1 | H | H | H | H | 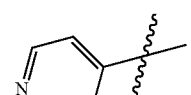 | Et | CH | CH | CH | CH | — | 508.0 |
| 50 | 1 | 1 | Me | H | H | H | 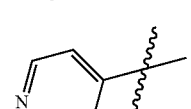 | Et | CH | CH | CH | CH | HCl | 494.0 |
| 51 | 1 | 1 | H | H | H | H |  |  | CH | CH | CH | CH | TFA | 506 |

-continued

| | | | | | | | | | | | | | |
|---|---|---|---|---|---|---|---|---|---|---|---|---|---|
| 52 | 1 | 1 | H | H | H | H | 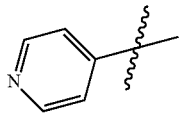 [SMILES: *c1ccncc1] | 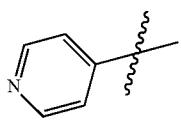 [SMILES: *c1ccncc1] | CH | CH | CH | CH | TFA | 520 |
| 53 | 1 | 1 | H | H | H | H | 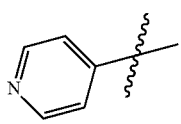 [SMILES: *c1ccncc1] | Et | CH | CH | CH | N | TFA | 481 |
| 54 | 1 | 1 | H | H | H | H | 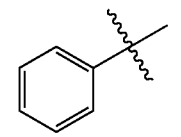 [SMILES: *c1ccccc1] | 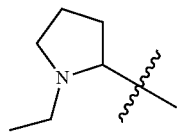 [SMILES: *C1CCCN1CC] | CH | CH | CH | CH | — | 524 |
| 55 | 1 | 3 | H | H | H | H | | Et | CH | CH | CH | CH | HCl | 507 |
| 56 | 1 | 2 | H | Me | H | H | | Et | CF | CH | CH | CH | — | 518.3 |

Pharmacological tests were conducted on the compounds according to the invention to determine their inhibitory effect on protein with tyrosine kinase activity. As an example, their inhibitory effects on the tyrosine kinase activity of PDGF-R and/or Flt-3 were measured in vitro in cellular models.

The inhibitory activity with respect to PDGF or Flt-3 receptors is given by the concentration that inhibits 50% of the proliferation activity of cells Baf3 tel/PDGF or MV4-11, respectively.

Measurement of Inhibition of the Tyrosine Kinase Activity of the Receptor to PDGF Beta (PDGF-R$\beta$) (Baf-3 tel/PDGFR$\beta$):

This test consists of evaluating the effects of the compounds on the tyrosine kinase activity of the PDGF beta receptor.

The inhibitory effect of the compounds according to the invention on the tyrosine kinase activity of the PDGF-R receptor was evaluated on the murine haematopoietic cell line BaF/3 transfected with a plasmid coding for the fusion protein Tel/PDGF-R beta. This fusion protein is found in chronic myeloid myelomonocytic leukaemias (CMML). It comprises the N-terminal part of the transcription factor Tel and the transmembrane and intracellular part of the PDGF-R beta receptor. This fusion protein is present in dimerized form (presence of an oligomerization domain in the N-terminal part of Tel) and accordingly leads to the constitutive activity of the kinase domain of PDGF-R beta. This line BaF3 Tel/PDGF has been described several times in the literature and notably in detail in the article of M CARROLL et al., PNAS, 1996, 93, 14845-14850, M CARROLL et al., Blood 2002, 99, 14845-14850.

The BaF3 Tel/PDGF cells are washed with phosphate buffer and seeded in 96-well plates, at a density of $5.10^4$ cells/ml (100 ml per well), in RPMI 1640 containing 10% of FCS, in the presence or absence of the test compounds. After incubation for 72 h, the viable cells are quantified by measurement of cellular ATP using the CellTiter-Glo® kit (Promega, Cat G7571). The cells are treated according to the instructions given by the supplier of the kit and the luminescence is measured with a Luminoskan (Ascent, Labsystem) with the following parameters: measurement: single; integration time: 1000 ms, lag time: 5 s.

It thus appears that the compounds according to the invention have an inhibitory activity on the tyrosine kinase activity of PDGF-R beta. This activity is given by the concentration that inhibits 50% of the proliferation of Baf3 tel/PDGF cells ($IC_{50}$). The $IC_{50}$ values of the compounds according to the invention are below 1.0 µM.

For example, compounds No. 2, 8, 9, 10, 14, 20, 27, 43, 50, 51, 52, 55 showed an $IC_{50}$ of 7.9, 2, 9.8, 2.5, 2.4, 8, 2, 1.4, 6.6, 8.9, 13.6, 5.9 nM respectively in the test for measuring the tyrosine kinase activity of the PDGF receptor.

In addition to their properties of inhibition of PDGF-R tyrosine kinase, it also appears that compounds according to the invention display properties of inhibition of the tyrosine kinase activity of the Flt-3 receptor, as described below.

Measurement of Inhibition of the Tyrosine Kinase Activity of the Flt-3 Receptor

The inhibitory effect of the compounds according to the invention on the tyrosine kinase activity of the Flt-3 receptor was evaluated on the MV4-11 cell line, a line established from a leukaemia of the AML type and bearing a constitutively active mutant Flt3ITD. The inhibitory activity is correlated with inhibition of cell growth, according to the protocols described by SPIEKERMANN, K. et al., Blood, 2003, 101, (4) 1494-1504 and O'FARRELL, A.-M. et al., Blood, 2003, 101, (9) 3597-3605.

The MV4-11 cells are washed with PBS buffer and seeded in 96-well plates, at a density of $1.10^5$ cells/ml (100 μl per well), in RPMI 1640 containing 10% of FCS, in the presence or absence of the test compounds. After incubation for 72 h, viable cells are quantified by measurement of cellular ATP using the CellTiter-Glo® kit (Promega, Cat G7571). The cells are treated according to the instructions given by the supplier of the kit and the luminescence is measured using a Luminoskan (Ascent, Labsystem) with the following parameters: measurement: single; integration time: 1000 ms, lag time: 5 s.

The inhibitory activity with respect to the Flt-3 receptor is given by the concentration that inhibits 50% of the proliferation of the MV4-11 cells. It thus appears that the compounds according to the invention have an inhibitory activity on the tyrosine kinase activity of the Flt-3 receptor with $IC_{50}$ values below 1.0 μM. For example, compounds No. 8, 20, 26, 27, 32, 42, 43, 50 showed an $IC_{50}$ of 52, 26, 95, 30, 69, 84, 19, 115 nM respectively, in the test for measuring the tyrosine kinase activity of the Flt-3 receptor.

The compounds according to the invention are therefore inhibitors of protein kinases, notably of the tyrosine kinase receptors PDGF alpha and beta and, for some of them, also of the Flt-3 tyrosine kinase receptor.

Thus, according to one of the objects of the present invention, the compounds of formula (I) display very interesting activity of inhibition of phosphorylation of the kinase domain of the PDGF-R beta receptor in BaF3 Tel/PDGF cells, induced by the inhibitory activity of the product present in the plasma of the treated animals.

The compounds according to the invention can therefore be used for preparing medicinal products, in particular medicinal products that are inhibitors of protein kinases.

The medicinal products are inhibitors of protein kinase, notably medicinal products that are inhibitors of the PDGF-R tyrosine kinase receptor and optionally of the Flt-3 tyrosine kinase receptor.

Thus, according to another of its aspects, the invention relates to medicinal products that comprise a compound of formula (I), or a salt of addition of the latter to a pharmaceutically acceptable acid, or a solvate of the compound of formula (I).

These medicinal products find application in therapeutics, notably in the treatment of diseases associated with the activity of protein kinases and notably proliferative diseases such as cancers with liquid tumours, chronic or acute leukaemias, lymphocytic lymphomas, Hodgkin's disease, myeloproliferative syndromes and myelodysplastic syndromes.

These medicinal products also find application in therapeutics in the treatment of proliferative diseases such as cancers with solid tumours comprising lung cancers (NSCLC), cancers of bone, pancreas, skin, Kaposi syndrome, intraocular melanomas, cancers associated with the sexual organs comprising cancer of the breast, uterus, cervix, ovary, endometrium, vagina, vulva, urethra, penis, prostate, carcinomas of the fallopian tubes, cancers of the gastrointestinal stromal tumour type (abbreviation: GIST) comprising cancers of the anal region, rectum, small intestine, colon, stomach, esophagus, cancers of endocrine glands, thyroid, parathyroid or adrenal glands, soft tissue sarcomas, Ewing sarcomas, osteosarcomas, dermatofibrosarcomas and other fibrosarcomas, cancers of the bladder or kidney, neoplasms of the central nervous system, tumours of the vertebral column and desmoids, gliomas of the brainstem and glioblastomas, pituitary adenomas and metastases thereof.

Another aspect of the invention comprises a combination between at least one compound according to the invention and at least one chemotherapy agent.

In fact, the compounds of the present invention can be used alone or mixed with at least one chemotherapy agent, which can be selected from cytotoxic agents and/or antiangiogens. For example, the antiangiogenic agents can be a compound that inhibits the kinase activity of VEGF-R or a compound that is an antagonist of a growth factor.

It is also possible to combine the compounds according to the invention with a radiation treatment.

The combinations of the compounds of the invention with the aforementioned chemotherapeutic agents and/or radiation are another subject of the present invention.

The aforementioned chemotherapeutic agents and/or radiation can be administered simultaneously, separately or sequentially. The treatment will be adapted by the practitioner according to the patient to be treated.

These medicinal products also find application in therapeutics, in the treatment of non-malignant proliferative diseases such as restenosis, atherosclerosis, thrombosis, heart failure, cardiac hypertrophy, pulmonary arterial hypertension, fibrosis, diabetic nephropathy, glomerulonephritis, chronic pyelonephritis, haemangiomas, auto-immune diseases such as psoriasis, sclerodermatitis, immunosuppression (transplant rejection for example), pathologies associated with the eye such as post-operative fibrosis or age-related macular degeneration.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the latter, or a solvate of said compound, as well as at least one pharmaceutically acceptable excipient.

Said excipients are selected depending on the pharmaceutical form and desired method of administration, from the usual excipients that are known by a person skilled in the art.

In the pharmaceutical compositions of the present invention for oral, sublingual, subcutaneous, intramuscular, intravenous, topical, intratracheal, intranasal, transdermal or rectal administration, the active principle of formula (I) above, or optionally a salt or solvate thereof, can be administered in the unit dosage form, mixed with conventional pharmaceutical excipients, to animals and to human beings for prophylaxis or treatment of the aforementioned disorders or diseases.

The appropriate unit dosage forms comprise the forms for administration by the oral route, such as tablets, soft or hard capsules, powders, granules and oral solutions or suspensions, forms for sublingual, buccal, intratracheal, intraocular, intranasal administration, administration by inhalation, forms for topical, transdermal, subcutaneous, intramuscular or intravenous administration, forms for rectal administration and implants. For topical application, the compounds according to the invention can be used in creams, gels, ointments or lotions.

As an example, a unit dosage form of a compound according to the invention in tablet form can comprise the following components:

| | |
|---|---:|
| Compound according to the invention | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

According to another of its aspects, the present invention also relates to a method of treatment of the aforementioned pathologies comprising the administration, to a patient, of an effective dose of a compound according to the invention or one of its pharmaceutically acceptable salts or solvates.

The invention claimed is:
1. A compound of formula (I):

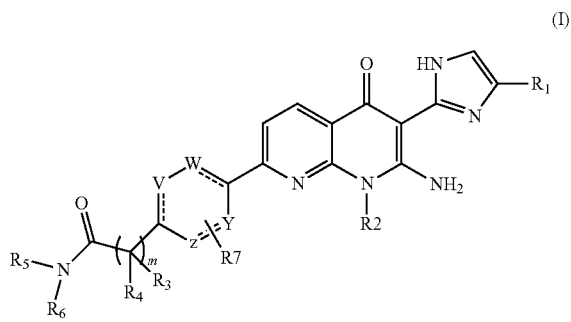

wherein:
R1 represents a hydrogen atom or $(C_1-C_4)$-alkyl;
R2 represents $—(CH_2)_{n'}$-B wherein:
n'=0, 1, 2, 3 or 4; and
B represents (i) $(C_3-C_5)$-cycloalkyl, (ii) $(C_1-C_4)$-alkyl optionally substituted with one or more fluorine atoms, or (iii) $(C_1-C_4)$-alkoxy;
Y, Z, V and W represent, independently of one another:
—CH—;
a carbon atom optionally substituted with R7, said R7 representing $(C_1-C_4)$-alkyl or a halogen atom;
a heteroatom selected from the group consisting of a nitrogen atom, a sulphur atom and an oxygen atom; or no atom,
wherein the ring comprising V, W, Y and Z is a ring comprising 5 or 6 ring members, the dotted lines in said ring indicate that the resultant ring is an aromatic ring, and said ring comprises 0, 1 or 2 heteroatoms;
R3 and R4 represent, independently of one another, groups that may be identical or different, R3 and R4 being selected from the group consisting of a hydrogen atom and linear $(C_1-C_4)$-alkyl; or R3 and R4 form, together with the carbon to which they are bound, $(C_3-C_5)$-cycloalkyl;
m is an integer equal to 1, 2, 3 or 4; and
R5 represents a hydrogen atom or $(C_1-C_4)$-alkyl, and R6 represents $—(CH_2)_n$-L wherein:
n=0, 1, 2 or 3, and
L is selected from the group consisting of:
an aryl comprising 6 carbon atoms;
a heteroaryl comprising between 5 and 6 ring members and comprising at least one heteroatom selected from the group consisting of nitrogen, oxygen and sulphur; and
a saturated heterocycle comprising 5, 6 or 7 ring members and comprising at least one heteroatom selected from the group consisting of nitrogen and oxygen, said heterocycle being optionally a lactam;
wherein said aryl, heteroaryl or heterocyclic group is optionally substituted with at least one substituent selected from the group consisting of (i) linear or branched $(C_1-C_4)$-alkyl, (ii) $(C_3-C_5)$-cycloalkyl, (iii) a halogen atom, (iv) aryl and (v) benzyl;
wherein when L is a heteroaryl or a heterocycle, said heteroaryl or heterocycle comprising at least one nitrogen atom, the heteroaryl or heterocycle can optionally be substituted with said substituent;
or R5 and R6 form, together with the nitrogen atom to which they are bound, a heterocyclic group, optionally substituted with at least
a heteroaryl, or
a $(C_1-C_3)$-alkyl, which is optionally substituted with a heterocycle comprising 5 or 6 atoms and comprising at least one heteroatom selected from the group consisting of nitrogen and oxygen, wherein when the $(C_1-C_3)$-alkyl is a heterocycle comprising at least one nitrogen atom, the heterocycle can optionally be substituted;
wherein said compound of formula (I) is in the form of a base or of an acid-addition salt thereof, or in the form of an enantiomer, diastereoisomer, or mixture thereof.

2. The compound according to claim 1, characterized in that R6 represents $—(CH_2)_n$-L wherein:
n=0, 1, 2 or 3, and
L is selected from the group consisting of:
a heteroaryl comprising 5 ring members and comprising (i) 2 heteroatoms selected, independently of one another, from the group consisting of nitrogen, oxygen and sulphur, or (ii) 3 heteroatoms selected, independently of one another, from the group consisting of nitrogen and sulphur,
a heteroaryl comprising 6 ring members and comprising 1 or 2 heteroatom(s),
a heterocycle comprising 5 ring members and comprising a heteroatom selected from the group consisting of nitrogen and oxygen, said heterocycle being optionally a lactam, and
a heterocycle comprising 6 ring members and comprising 2 heteroatoms selected from the group consisting of nitrogen and oxygen,
said heteroaryl or heterocycle being optionally substituted with at least one substituent selected from the group consisting of (i) linear or branched $(C_1-C_4)$-alkyl, (ii) $(C_3-C_5)$-cycloalkyl, (iii) a halogen atom, (iv) aryl and (v) benzyl,
wherein when L is a heteroaryl or a heterocycle comprising at least one nitrogen atom, the heteroaryl or heterocycle can optionally be substituted with said substituent.

3. The compound according to claim 1, wherein L is:
a heteroaryl comprising 6 ring members selected from the group consisting of pyridine, pyrazine, pyridazine, and pyrimidine;
an aryl such as phenyl;
a heteroaryl comprising 5 ring members selected from the group consisting of thiazole, imidazole, pyrazole, isoxazole and 1,3,4-thiadiazole;
a saturated heterocycle comprising 5 ring members selected from the group consisting of pyrrolidine, tetrahydrofuran and 2-oxo-pyrrolidine; or
a saturated heterocycle comprising 6 ring members selected from the group consisting of morpholine, piperazine, and piperidine;

wherein said aryl, heteroaryl or heterocyclic group is optionally substituted with at least one substituent selected from (i) linear or branched ($C_1$-$C_4$)-alkyl, (ii) ($C_3$-$C_5$)-cycloalkyl, and (iii) aryl, and further wherein when L is a heteroaryl or a heterocycle comprising at least one nitrogen atom, the heteroaryl or a heterocycle can optionally be substituted with said substituent.

4. The compound according to claim 1, wherein L is selected from the group consisting of:
   pyridine, optionally substituted with at least one linear or branched ($C_1$-$C_4$)-alkyl;
   morpholine, optionally substituted with at least (i) ($C_3$-$C_5$)-cycloalkyl or (ii) linear or branched ($C_1$-$C_4$)-alkyl;
   pyrrolidine, optionally substituted with at least (i) linear or branched ($C_1$-$C_4$)-alkyl, or (ii) benzyl;
   thiazole, optionally substituted with at least (i) linear or branched ($C_1$-$C_4$)-alkyl, or (ii) a chlorine atom;
   imidazole, optionally substituted with at least one linear or branched ($C_1$-$C_4$)-alkyl;
   2-oxo-pyrrolidine;
   1,3,4-thiadiazole, optionally substituted with at least (i) linear or branched ($C_1$-$C_4$)-alkyl, or (ii) a ($C_3$-$C_5$)-cycloalkyl;
   isoxazole, optionally substituted with at least one linear or branched ($C_1$-$C_4$)-alkyl;
   pyrazole, optionally substituted with at least one linear or branched ($C_1$-$C_4$)-alkyl;
   pyrazine;
   isothiazole, optionally substituted with at least one linear or branched ($C_1$-$C_4$)-alkyl;
   phenyl; and
   tetrahydrofuran,
wherein when L is a heteroaryl or a heterocycle comprising at least one nitrogen atom, the heteroaryl or heterocycle can optionally be substituted.

5. The compound according to claim 1, wherein R5 represents a hydrogen atom or methyl.

6. The compound according to claim 1, wherein:
   m is equal to 1 or 3, and/or
   R3 and R4 represent, independently of one another, groups that may be identical or different, R3 and R4 being selected from the group consisting of a hydrogen atom and methyl.

7. The compound according to claim 1, wherein Y, Z, V and W represent, independently of one another:
   —CH—;
   a carbon atom substituted with a group R7, said group R7 representing ($C_1$-$C_4$)-alkyl or a fluorine atom; or
   a heteroatom selected from the group consisting of a nitrogen atom, a sulphur atom and an oxygen atom.

8. The compound according to claim 1, wherein R1 represents a hydrogen atom or methyl.

9. The compound according to claim 1, wherein R2 represents —$(CH_2)_n$-B wherein:
   n'=0, 1 or 3; and/or
   B represents (i) ($C_3$-$C_5$)-cycloalkyl, (ii) ($C_1$-$C_4$)-alkyl or (iii) a ($C_1$-$C_4$)-alkoxy.

10. The compound according to claim 1, wherein R5 and R6 form, together with the nitrogen atom to which they are bound, a heterocyclic group, optionally substituted with at least
   a heteroaryl; or
   ($C_1$-$C_3$)alkyl, which is optionally substituted with a heterocycle comprising 5 or 6 atoms and comprising at least one heteroatom selected from the group consisting of nitrogen and oxygen.

11. The compound according to claim 1, wherein the compound is in the form of a base or a salt of addition to an acid such as hydrochloric acid or trifluoroacetic acid.

12. The compound according to claim 1, wherein the compound is selected from the group consisting of:
   2-{4-[7-Amino-8-ethyl-6-(1H-imidazol-2-yl)-5-oxo-5,8-dihydro-[1,8]naphthyridin-2-yl]-phenyl}-N-pyridin-2-yl-acetamide;
   2-{6-[7-Amino-8-ethyl-6-(1H-imidazol-2-yl)-5-oxo-5,8-dihydro-[1,8]naphthyridin-2-yl]-pyridin-3-yl}-N-pyridin-2-yl-acetamide;
   2-{4-[7-Amino-8-ethyl-6-(1H-imidazol-2-yl)-5-oxo-5,8-dihydro-[1,8]naphthyridin-2-yl]-phenyl}-N-(4-cyclopropyl-morpholin-3-ylmethyl)-acetamide;
   2-{4-[7-Amino-8-ethyl-6-(1H-imidazol-2-yl)-5-oxo-5,8-dihydro-[1,8]naphthyridin-2-yl]-phenyl}-N-(4-isopropyl-morpholin-3-ylmethyl)-acetamide;
   2-Amino-1-ethyl-3-(1H-imidazol-2-yl)-7-{-4-[2-oxo-2-((S)-2-pyrrolidin-1-ylmethyl-pyrrolidin-1-yl)-ethyl]-phenyl}-1H-[1,8]naphthyridin-4-one;
   2-{4-[7-Amino-8-ethyl-6-(1H-imidazol-2-yl)-5-oxo-5,8-dihydro-[1,8]naphthyridin-2-yl]-phenyl}-N-(2-pyridin-4-yl-ethyl)-acetamide;
   2-{4-[7-Amino-8-ethyl-6-(1H-imidazol-2-yl)-5-oxo-5,8-dihydro-[1,8]naphthyridin-2-yl]-phenyl}-N-methyl-N-(2-pyridin-4-yl-ethyl)-acetamide;
   2-{4-[7-Amino-8-ethyl-6-(1H-imidazol-2-yl)-5-oxo-5,8-dihydro-[1,8]naphthyridin-2-yl]-phenyl}-N-(5-methyl-thiazol-2-yl)-acetamide;
   2-{4-[7-Amino-8-ethyl-6-(1H-imidazol-2-yl)-5-oxo-5,8-dihydro-[1,8]naphthyridin-2-yl]-3-methyl-phenyl}-N-(1-ethyl-pyrrolidin-2-ylmethyl)-acetamide;
   2-{4-[7-Amino-8-ethyl-6-(1H-imidazol-2-yl)-5-oxo-5,8-dihydro-[1,8]naphthyridin-2-yl]-phenyl}-N-(6-methyl-pyridin-3-yl)-acetamide;
   2-{4-[7-Amino-8-ethyl-6-(1H-imidazol-2-yl)-5-oxo-5,8-dihydro-[1,8]naphthyridin-2-yl]-phenyl}-N-(1,3-dimethyl-1H-pyrazol-4-ylmethyl)-acetamide;
   2-{4-[7-Amino-8-ethyl-6-(1H-imidazol-2-yl)-5-oxo-5,8-dihydro-[1,8]naphthyridin-2-yl]-phenyl}-N-thiazol-2-ylmethyl-acetamide;
   2-{4-[7-Amino-8-ethyl-6-(1H-imidazol-2-yl)-5-oxo-5,8-dihydro-[1,8]naphthyridin-2-yl]-phenyl}-N-(5-oxo-pyrrolidin-2-ylmethyl)-acetamide;
   2-{4-[7-Amino-8-ethyl-6-(1H-imidazol-2-yl)-5-oxo-5,8-dihydro-[1,8]naphthyridin-2-yl]-phenyl}-N-(5-methyl-[1,3,4]thiadiazol-2-yl)-acetamide;
   2-{4-[7-Amino-8-ethyl-6-(1H-imidazol-2-yl)-5-oxo-5,8-dihydro-[1,8]naphthyridin-2-yl]-phenyl}-N-[1,3,4]thiadiazol-2-yl-acetamide;
   2-{4-[7-Amino-8-ethyl-6-(1H-imidazol-2-yl)-5-oxo-5,8-dihydro-[1,8]naphthyridin-2-yl]-phenyl}-N-(3-methyl-isoxazol-5-yl)-acetamide;
   2-{4-[7-Amino-8-ethyl-6-(1H-imidazol-2-yl)-5-oxo-5,8-dihydro-[1,8]naphthyridin-2-yl]-phenyl}-N-[2-(1-methyl-pyrrolidin-2-yl)-ethyl]-acetamide;
   2-{4-[7-Amino-8-ethyl-6-(1H-imidazol-2-yl)-5-oxo-5,8-dihydro-[1,8]naphthyridin-2-yl]-phenyl}-N-(4-methyl-thiazol-2-yl)-acetamide;
   2-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-acetamide;
   2-{4-[7-Amino-8-ethyl-6-(1H-imidazol-2-yl)-5-oxo-5,8-dihydro-[1,8]naphthyridin-2-yl]-phenyl}-N-(5-cyclopropyl-[1,3,4]thiadiazol-2-yl)-acetamide;

2-{4-[7-Amino-8-ethyl-6-(1H-imidazol-2-yl)-5-oxo-5,8-dihydro-[1,8]naphthyridin-2-yl]-phenyl}-N-(2-pyridin-3-yl-ethyl)-acetamide;
2-{4-[7-Amino-8-ethyl-6-(1H-imidazol-2-yl)-5-oxo-5,8-dihydro-[1,8]naphthyridin-2-yl]-phenyl}-N-(2,5-dimethyl-2H-pyrazol-3-ylmethyl)-acetamide;
2-{4-[7-Amino-8-ethyl-6-(1H-imidazol-2-yl)-5-oxo-5,8-dihydro-[1,8]naphthyridin-2-yl]-phenyl}-N-(1-methyl-1H-imidazol-4-ylmethyl)-acetamide;
2-{4-[7-Amino-8-ethyl-6-(1H-imidazol-2-yl)-5-oxo-5,8-dihydro-[1,8]naphthyridin-2-yl]-phenyl}-N-pyrazin-2-yl-acetamide;
2-{4-[7-Amino-8-ethyl-6-(1H-imidazol-2-yl)-5-oxo-5,8-dihydro-[1,8]naphthyridin-2-yl]-phenyl}-N-(2-pyridin-2-yl-ethyl)-acetamide;
2-{4-[7-Amino-8-ethyl-6-(1H-imidazol-2-yl)-5-oxo-5,8-dihydro-[1,8]naphthyridin-2-yl]-phenyl}-N-(5-chloro-thiazol-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-(3,4-dimethyl-isoxazol-5-yl)-acetamide;
2-{4-[7-Amino-8-ethyl-6-(1H-imidazol-2-yl)-5-oxo-5,8-dihydro-[1,8]naphthyridin-2-yl]-phenyl}-N-(2-methyl-pyridin-4-yl)-acetamide;
2-{4-[7-Amino-8-ethyl-6-(1H-imidazol-2-yl)-5-oxo-5,8-dihydro-[1,8]naphthyridin-2-yl]-phenyl}-N-pyrazin-2-ylmethyl-acetamide;
2-{4-[7-Amino-8-ethyl-6-(1H-imidazol-2-yl)-5-oxo-5,8-dihydro-[1,8]naphthyridin-2-yl]-phenyl}-N-(5-ethyl-[1,3,4]thiadiazol-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-(tetrahydro-furan-2-ylmethyl)-acetamide;
2-{4-[7-Amino-8-ethyl-6-(1H-imidazol-2-yl)-5-oxo-5,8-dihydro-[1,8]naphthyridin-2-yl]-phenyl}-N-(3-methyl-pyridin-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-(4-methyl-pyridin-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-(4,6-dimethyl-pyridin-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-(6-methyl-pyridin-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-pyridin-3-ylmethyl-acetamide;
2-{4-[7-Amino-8-ethyl-6-(1H-imidazol-2-yl)-5-oxo-5,8-dihydro-[1,8]naphthyridin-2-yl]-phenyl}-N-(2-ethyl-2H-pyrazol-3-yl)-acetamide;
2-{4-[7-Amino-8-ethyl-6-(1H-imidazol-2-yl)-5-oxo-5,8-dihydro-[1,8]naphthyridin-2-yl]-phenyl}-N-(3-methyl-isothiazol-5-yl)-acetamide;
2-Amino-1-ethyl-3-(1H-imidazol-2-yl)-7-{-4-[2-oxo-2-(2-pyridin-3-yl-pyrrolidin-1-yl)-ethyl]-phenyl}-1H-[1,8]naphthyridin-4-one;
2-{4-[7-Amino-8-ethyl-6-(1H-imidazol-2-yl)-5-oxo-5,8-dihydro-[1,8]naphthyridin-2-yl]-phenyl}-N-(1-benzyl-pyrrolidin-3-yl)-acetamide;
2-{4-[7-Amino-8-ethyl-6-(1H-imidazol-2-yl)-5-oxo-5,8-dihydro-[1,8]naphthyridin-2-yl]-phenyl}-N-[(S)-1-(tetrahydro-furan-2-yl)methyl]-acetamide;
2-{4-[7-Amino-8-ethyl-6-(1H-imidazol-2-yl)-5-oxo-5,8-dihydro-[1,8]naphthyridin-2-yl]-phenyl}-N-(4-methyl-pyridin-3-yl)-acetamide;
2-{4-[7-Amino-8-ethyl-6-(1H-imidazol-2-yl)-5-oxo-5,8-dihydro-[1,8]naphthyridin-2-yl]-phenyl}-N-(4-ethyl-pyridin-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-ethyl-N-pyridin-4-ylmethyl-acetamide;
2-{4-[7-Amino-8-ethyl-6-(1H-imidazol-2-yl)-5-oxo-5,8-dihydro-[1,8]naphthyridin-2-yl]-phenyl}-N-(6-ethyl-pyridin-2-yl)-acetamide;
2-{4-[7-Amino-8-ethyl-6-(1H-imidazol-2-yl)-5-oxo-5,8-dihydro-[1,8]naphthyridin-2-yl]-phenyl}-N-benzyl-acetamide;
2-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-propionamide;
4-[7-Amino-8-ethyl-6-(1H-imidazol-2-yl)-5-oxo-5,8-dihydro-[1,8]naphthyridin-2-yl]-N-pyridin-4-ylmethyl-benzamide;
4-{4-[7-Amino-8-ethyl-6-(1H-imidazol-2-yl)-5-oxo-5,8-dihydro-[1,8]naphthyridin-2-yl]-phenyl}-N-pyridin-4-ylmethyl-butyramide;
2-{4-[7-Amino-8-ethyl-6-(4-methyl-1H-imidazol-2-yl)-5-oxo-5,8-dihydro-[1,8]naphthyridin-2-yl]-phenyl}-N-pyridin-4-ylmethyl-acetamide;
2-{4-[7-Amino-8-cyclopropylmethyl-6-(1H-imidazol-2-yl)-5-oxo-5,8-dihydro-[1,8]naphthyridin-2-yl]-phenyl}-N-pyridin-4-ylmethyl-acetamide;
2-{4-[7-Amino-8-cyclopentyl-6-(1H-imidazol-2-yl)-5-oxo-5,8-dihydro-[1,8]naphthyridin-2-yl]-phenyl}-N-pyridin-4-ylmethyl-acetamide (compound 52);
2-{5-[7-Amino-8-ethyl-6-(1H-imidazol-2-yl)-5-oxo-5,8-dihydro-[1,8]naphthyridin-2-yl]-pyridin-2-yl}-N-pyridin-4-ylmethyl-acetamide;
2-{4-[7-Amino-6-(1H-imidazol-2-yl)-8-(3-methoxy-propyl)-5-oxo-5,8-dihydro-[1,8]naphthyridin-2-yl]-phenyl}-N-pyridin-4-ylmethyl-acetamide;
2-{4-[7-Amino-8-ethyl-6-(1H-imidazol-2-yl)-5-oxo-5,8-dihydro-[1,8]naphthyridin-2-yl]-phenyl}-N-(3-phenyl-propyl)-acetamide; and
2-{4-[7-Amino-8-ethyl-6-(1H-imidazol-2-yl)-5-oxo-5,8-dihydro-[1,8]naphthyridin-2-yl]-2-fluoro-phenyl}-N-(1-ethyl-pyrrolidin-2-ylmethyl)-acetamide.

13. A process for preparing the compound according to claim 1, comprising the step of reacting a compound of formula (VII):

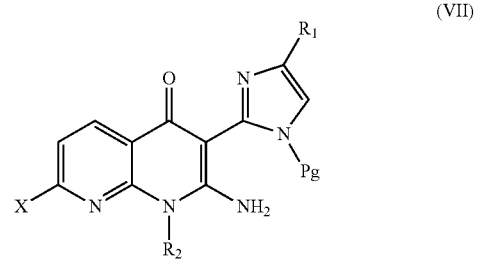

wherein Pg represents a protecting group and X represents a halogen atom, with a boronic acid or a boronic ester of pinacol of formula (IXa):

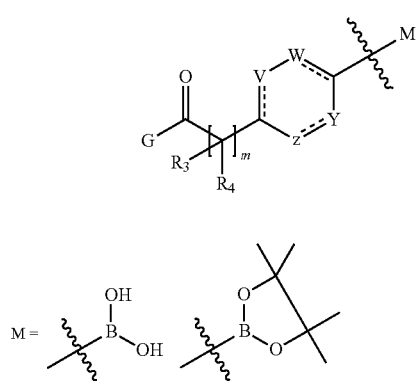
(IXa)

wherein G represents —NR5R6 or G represents —OEt;
to obtain respectively a compound of formula (X):

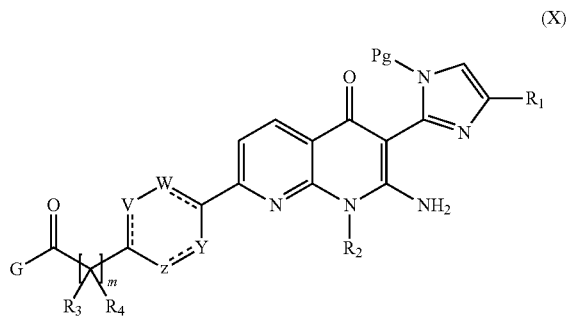
(X)

wherein G represents a —NR5R6 and Pg is a protecting group;
or a compound of formula (XI):

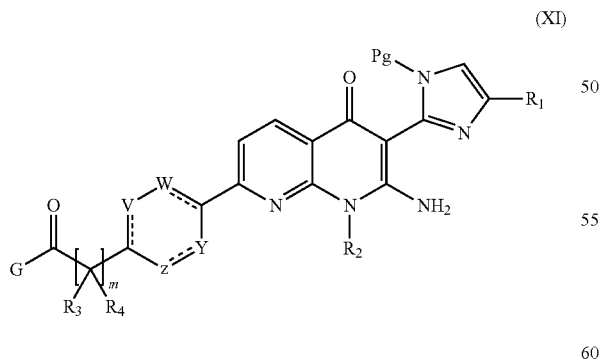
(XI)

wherein G represents —OEt and Pg is a protecting group;
and wherein m, R1, R2, R3, R4, R5, R6, V, W, Y and Z are as defined in claim 1.

14. A process for preparing the compound according to claim 1, comprising the step of reacting a compound of formula (VIII):

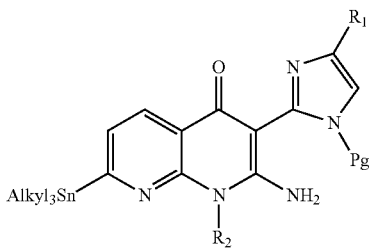
(VIII)

wherein Pg represents a protecting group,
with an aryl or heteroaryl halide of formula (IXb):

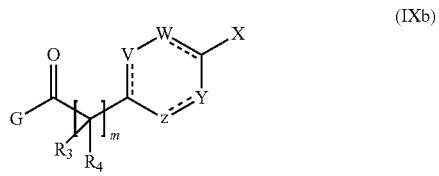
(IXb)

wherein G represents —OEt or —NR5R6 and X represents a halogen atom;
to obtain a compound of formula (X):

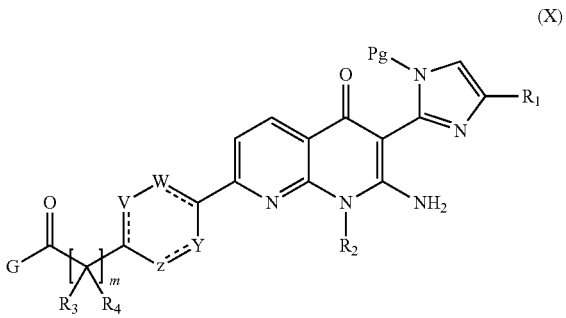
(X)

wherein G represents —NR5R6 and Pg is protecting group,
or a compound of formula (XI):

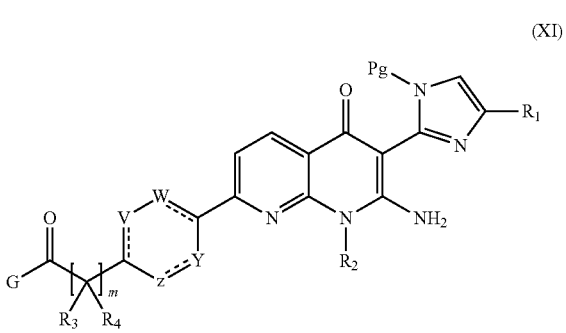
(XI)

wherein G represents —OEt,
and wherein m, R1, R2, R3, R4, R5, R6, V, W, Y and Z are as defined in claim 1.

15. The process according to claim 13, comprising saponifying and then peptide coupling with the amine HNR5R6 a compound of formula (XI) wherein G represents —OEt, to obtain a compound of formula (XIII):

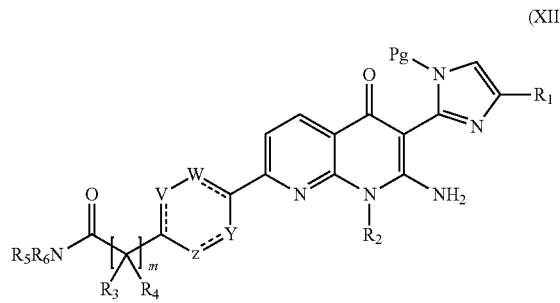

(XIII)

wherein Pg represents a protecting group and wherein m, R1, R2, R3, R4, R5, R6, V, W, Y and Z are as defined in claim 1.

16. A pharmaceutical composition comprising the compound according to claim 1 and at least one pharmaceutically acceptable excipient.

17. A method of inhibiting the tyrosine kinase activity of PDGF-R or Flt-3, comprising administering to a subject in need thereof a therapeutically effective amount of the compound according to claim 1.

18. The method according to claim 17, wherein the tyrosine kinase activity of PDGF-R is the tyrosine kinase activity of PDGF-R beta.

19. A method for treating a chronic or acute leukaemia, a lymphocytic lymphoma, Hodgkin's disease, a myeloproliferative syndrome or myelodysplastic syndrome, comprising administering to a subject in need thereof a therapeutically effective amount of the compound according to claim 1.

20. A method for treating a lung cancer (NSCLC), bone cancer, pancreatic cancer, skin cancer, Kaposi syndrome, intraocular melanoma, breast cancer, uterine cancer, cervical cancer, ovarian cancer, cancer of the endometrium, cancer of the vagina, cancer of the vulva, cancer of the urethra, cancer of the penis, prostate cancer, carcinoma of the fallopian tubes, cancer of the gastrointestinal stromal tumour type (abbreviation: GIST) comprising cancer of the anal region, rectal cancer, cancer of the small intestine, colon cancer, stomach cancer, esophageal cancer, cancer of the endocrine glands, thyroid cancer, cancer of the parathyroid or adrenal glands, a soft tissue sarcoma, Ewing sarcoma, an osteosarcoma, a dermatofibrosarcoma or other fibrosarcomas, cancer of the bladder or kidney, a neoplasm of the central nervous system, a tumour of the vertebral column or desmoids, a glioma of the brainstem or glioblastomas, a pituitary adenoma, or metastases thereof, comprising administering to a subject in need thereof a therapeutically effective amount of the compound according to claim 1.

21. The process according to claim 14, comprising saponifying and then peptide coupling with the amine HNR5R6 a compound of formula (XI) wherein G represents —OEt, to obtain a compound of formula (XIII):

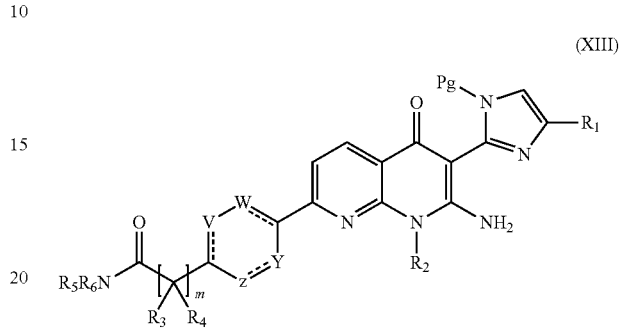

(XIII)

wherein Pg represents a protecting group and wherein m, R1, R2, R3, R4, R5, R6, V, W, Y and Z are as defined in claim 1.

22. The compound according to claim 1, wherein Y, Z, V and W represent, independently of one another:
—CH—;
a carbon atom substituted with a group R7, said group R7 representing $(C_1$-$C_4)$-alkyl or a fluorine atom; or
a nitrogen atom.

23. The compound according to claim 1, wherein R5 and R6 form, together with the nitrogen atom to which they are bound, a heterocyclic group, optionally substituted with at least
a pyridine; or
$(C_1$-$C_3)$alkyl, which is optionally substituted with a heterocycle comprising 5 or 6 atoms and comprising at least one heteroatom selected from the group consisting of nitrogen and oxygen.

24. The compound according to claim 1, wherein R5 and R6 form, together with the nitrogen atom to which they are bound, a heterocyclic group, optionally substituted with at least
a heteroaryl; or
a C1alkyl group substituted with a heterocycle comprising 5 atoms including a nitrogen atom.

* * * * *